US010058362B2

(12) United States Patent
Vasta

(10) Patent No.: US 10,058,362 B2
(45) Date of Patent: Aug. 28, 2018

(54) ORTHOPEDIC BONE FIXATION ASSEMBLY

(71) Applicant: Gramercy Extremity Orthopedics, LLC, Richardson, TX (US)

(72) Inventor: Paul Vasta, Richardson, TX (US)

(73) Assignee: Gramercy Extremity Orthopedics LLC, Richardson, TX (US)

( * ) Notice: Subject to any disclaimer, the term of this patent is extended or adjusted under 35 U.S.C. 154(b) by 91 days.

(21) Appl. No.: 15/160,604

(22) Filed: May 20, 2016

(65) Prior Publication Data

US 2017/0333098 A1   Nov. 23, 2017

Related U.S. Application Data

(60) Provisional application No. 62/187,766, filed on Jul. 1, 2015, provisional application No. 62/165,419, filed on May 22, 2015, provisional application No. 62/165,582, filed on May 22, 2015.

(51) Int. Cl.
*A61B 17/80* (2006.01)
*A61B 17/17* (2006.01)

(52) U.S. Cl.
CPC .......... *A61B 17/8047* (2013.01); *A61B 17/80* (2013.01); *A61B 17/8033* (2013.01); *A61B 17/8052* (2013.01); *A61B 17/8057* (2013.01); *A61B 17/1728* (2013.01)

(58) Field of Classification Search
CPC . A61B 17/80; A61B 17/8033; A61B 17/8047; A61B 17/8052; A61B 17/8057
See application file for complete search history.

(56) References Cited

U.S. PATENT DOCUMENTS

| 4,388,921 | A | * | 6/1983 | Sutter ............... A61B 17/8047 |
| | | | | 411/537 |
| 5,520,690 | A | | 5/1996 | Errico et al. |
| 5,607,426 | A | | 3/1997 | Ralph et al. |
| 5,709,686 | A | | 1/1998 | Talos et al. |
| 5,735,853 | A | | 4/1998 | Olerud |
| 5,954,722 | A | | 9/1999 | Bono |
| 6,322,562 | B1 | | 11/2001 | Wolter |

(Continued)

FOREIGN PATENT DOCUMENTS

| WO | 2007093855 A1 | 8/2007 | |
| WO | 2012174385 A2 | 12/2012 | |
| WO | WO 2017100196 A1 * | 6/2017 | ............. A61B 17/56 |

*Primary Examiner* — Larry E Waggle, Jr.
(74) *Attorney, Agent, or Firm* — Panitch Schwarze Belisario & Nadel LLP

(57) ABSTRACT

An orthopedic fixation assembly for connecting to a bone includes a fixation plate having a hole, an insert securable to the hole and a screw securable to the insert. The fixation plate includes a shoulder recessed from its upper surface and an aperture. The insert includes a base portion and a flange extending laterally from an upper end of the base portion. The insert defines an insert central axis extending in a direction generally perpendicular to the flange. The screw has a screw head and the base portion has an insert hole with machined internal threads for engaging the screw. The insert hole defines an insert hole central axis extending in a direction at an offset angle relative to the insert central axis. The aperture of the fixation plate is dimensioned to receive the base portion of the insert and the recessed shoulder is dimensioned to receive the flange.

13 Claims, 12 Drawing Sheets

(56) References Cited

U.S. PATENT DOCUMENTS

| | | | |
|---|---|---|---|
| 6,893,443 B2 | 5/2005 | Frigg et al. | |
| 6,955,677 B2 | 10/2005 | Dahners | |
| 6,974,461 B1 | 12/2005 | Wolter | |
| 7,001,389 B1 | 2/2006 | Navarro et al. | |
| 7,637,928 B2 | 12/2009 | Fernandez | |
| 8,075,561 B2 | 12/2011 | Wolter | |
| 8,114,140 B2 | 2/2012 | Derouet | |
| 8,142,485 B2 * | 3/2012 | Buhren | A61B 17/8033 606/289 |
| 8,343,196 B2 | 1/2013 | Schneider | |
| 8,486,116 B2 | 7/2013 | Heilman | |
| 8,500,784 B2 | 8/2013 | Hulliger et al. | |
| 8,574,268 B2 | 11/2013 | Chan et al. | |
| 8,728,129 B2 | 5/2014 | Fritzinger et al. | |
| 8,771,324 B2 | 7/2014 | Black et al. | |
| 8,870,931 B2 | 10/2014 | Dahners et al. | |
| 8,951,291 B2 | 2/2015 | Impellizzeri | |
| 9,039,745 B2 | 5/2015 | Fritzinger | |
| 9,113,970 B2 * | 8/2015 | Lewis | A61B 17/1728 |
| 2009/0018588 A1 | 1/2009 | Eckhof et al. | |
| 2009/0248087 A1 | 10/2009 | Lewis et al. | |
| 2010/0174324 A1 | 7/2010 | Derouet | |
| 2011/0015682 A1 | 1/2011 | Lewis et al. | |
| 2011/0202092 A1 | 8/2011 | Frigg et al. | |
| 2012/0059385 A1 | 3/2012 | Lewis et al. | |
| 2014/0214092 A1 | 7/2014 | Wolter | |

* cited by examiner

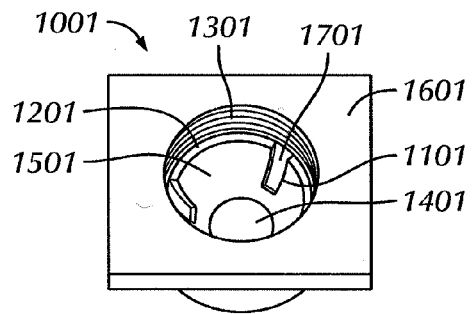
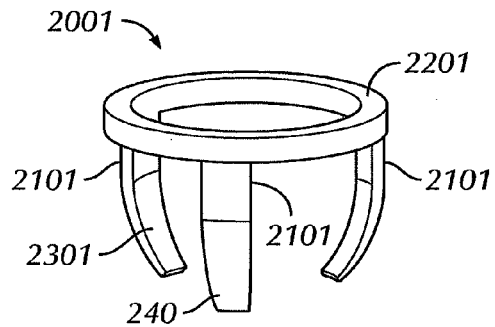
FIG. 9  FIG. 10
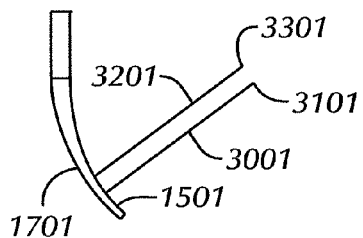
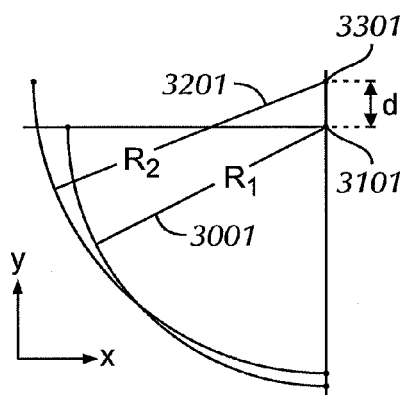
FIG. 11A  FIG. 11B
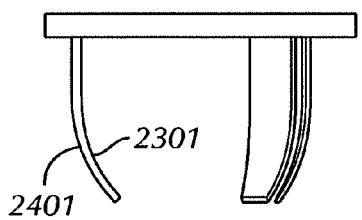
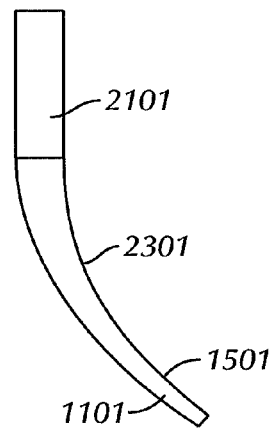
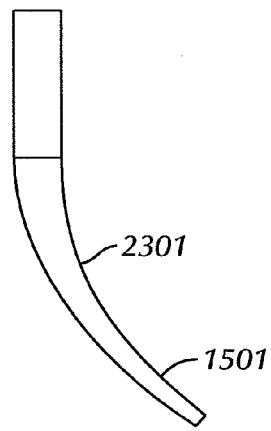
FIG. 12  FIG. 13A  FIG. 13B

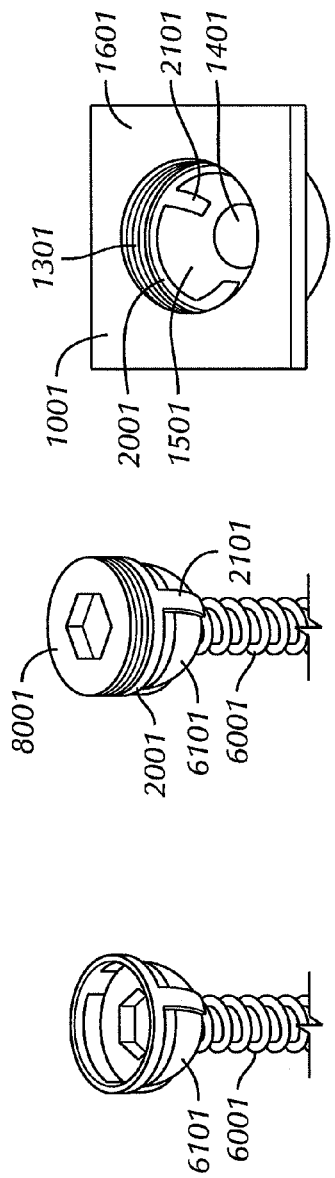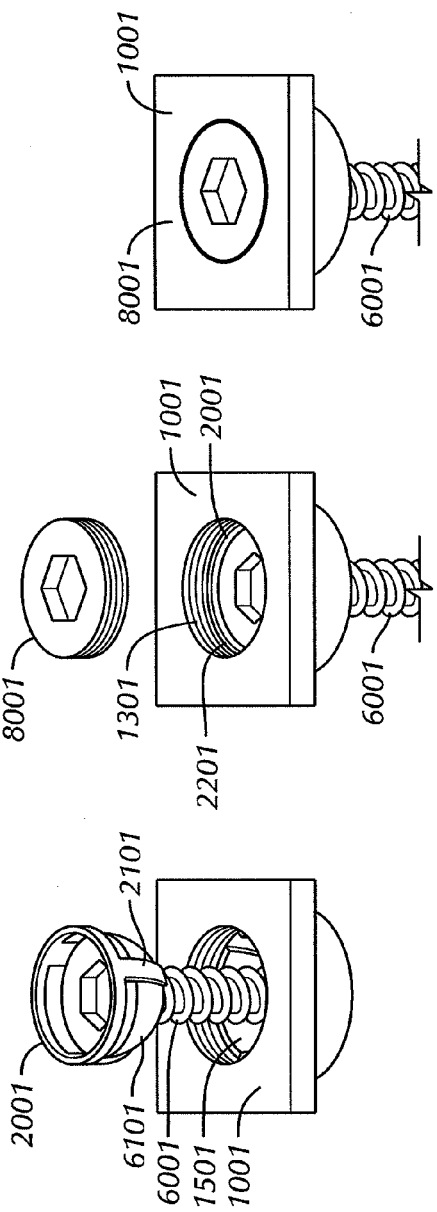

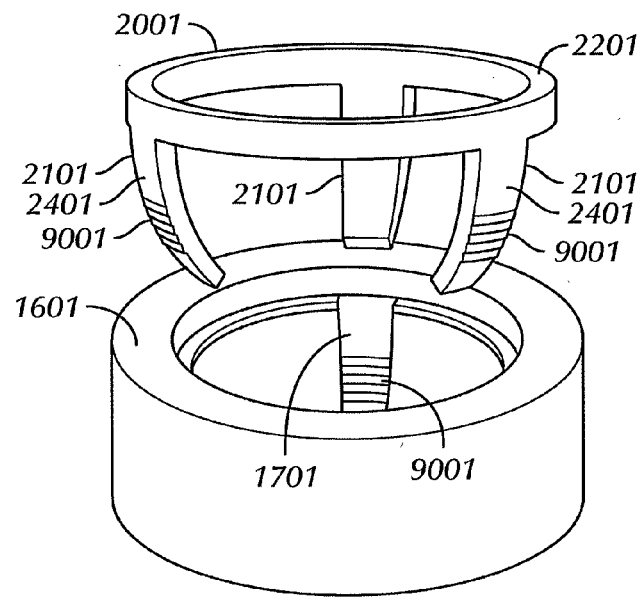
FIG. 17
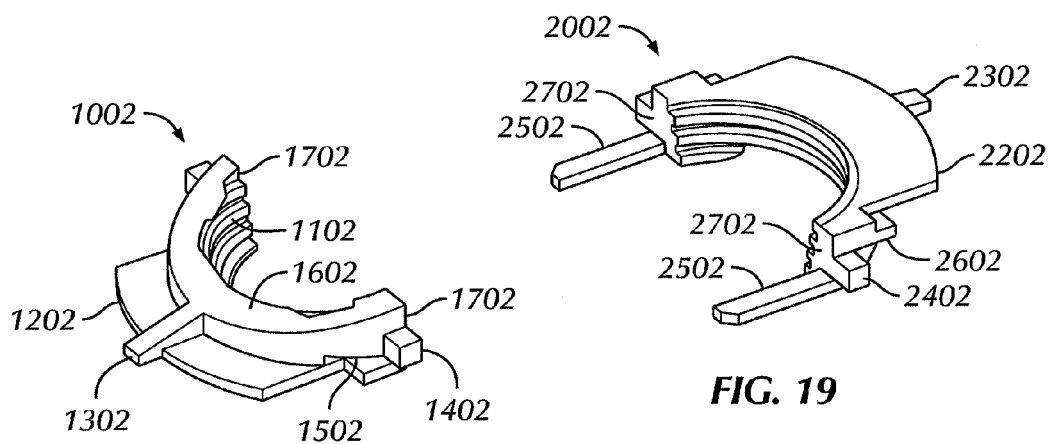
FIG. 18
FIG. 19

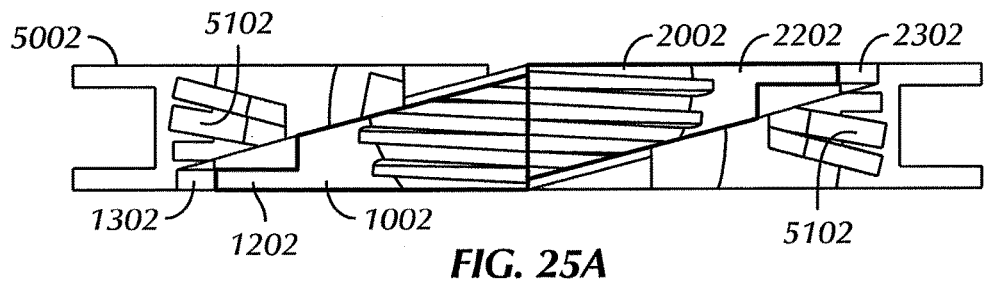
*FIG. 25A*
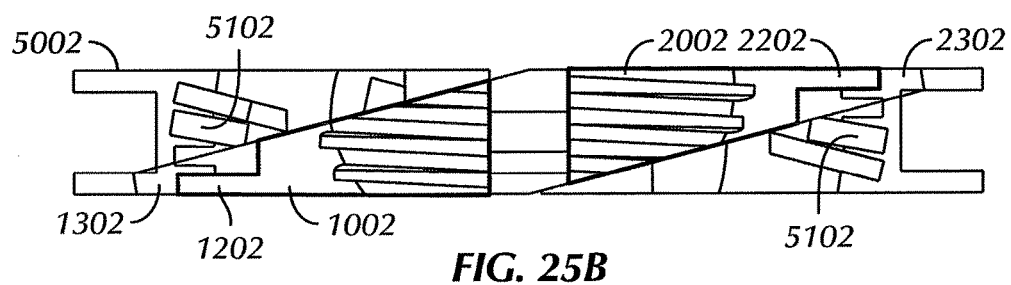
*FIG. 25B*
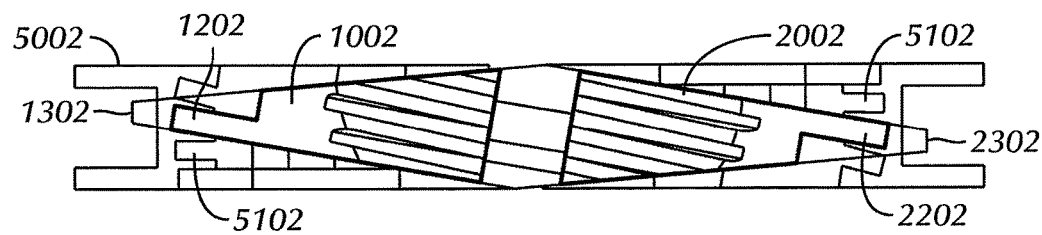
*FIG. 25C*
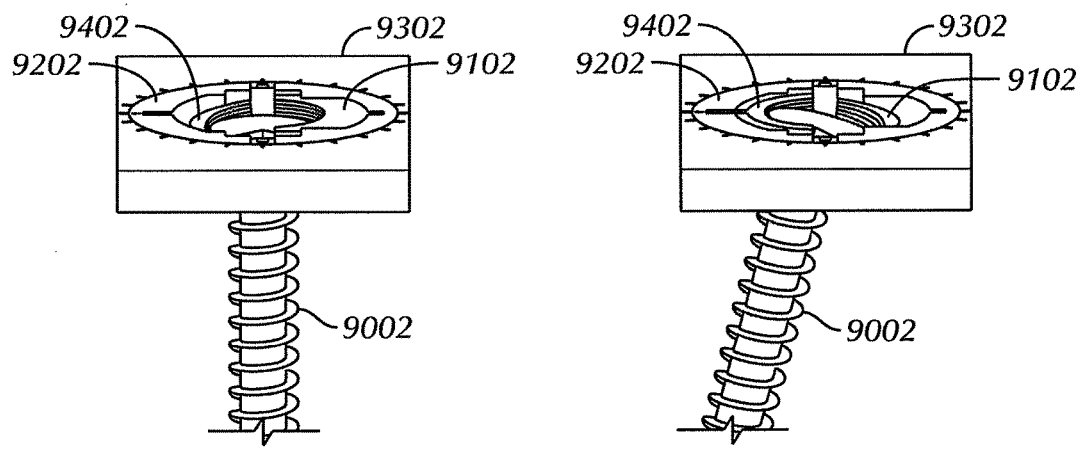
*FIG. 26A*     *FIG. 26B*

ORTHOPEDIC BONE FIXATION ASSEMBLY

CROSS REFERENCE TO RELATED APPLICATIONS

This application claims priority to U.S. Provisional Patent Application No. 62/165,419, filed on May 22, 2015, entitled "Orthopedic Incremental Screw Lock", U.S. Provisional Patent Application No. 62/165,582, filed on May 22, 2015, entitled "Orthopedic Variable Screw Lock" and U.S. Provisional Patent Application No. 62/187,766, filed Jul. 1, 2015, entitled "Orthopedic Incremental Screw Lock Mechanism", the entire contents of each of which are incorporated by reference herein.

BACKGROUND OF THE INVENTION

The present invention relates to orthopedic implants for use in repairing fractured bones or bones that have undergone a surgical procedure for therapeutic purposes, e.g., deformity correction, reconstruction, arthrodesis, etc. The implants described herein refer more specifically to an orthopedic bone fixation plate and screw construct. In situations where the bone fixation occurs near a joint and the surgeon desires to angle the screw to avoid encroachment into the joint, where the surgeon wishes to intentionally angle a screw to cross a fracture gap or joint in order to achieve fusion, or other surgical applications where intentional screw angulation is useful, it is desirable to insert the fixation screw at an angle offset from the central axis of the screw hole in the bone plate and an orientation directed radially about the circumference of the hole. In addition, there are clinical circumstances in which rigidity of fixation is desired, specifically between the screw and the plate, where it is desirable for forces acting on the bone to be counteracted in part or in whole by the screw-plate construct. In these situations, it is preferred to provide a means for rigidly locking the screw to the plate where the shaft of the screw is substantially fixed at various angles to the central axis and orientations about the circumference of the screw hole. This type of plate/screw construct may be referred to in orthopedics as variable-angle locking.

Variable angle locking in orthopedic applications may utilize various mechanical designs to secure the head of the bone screw to the plate hole. These designs may include cross-threading, self-tapping, and frictional "crush-lock" features that provide a degree of rigidity between the plate and screw. However, each of these designs is limited in the strength of the interface between the screw head and the plate due to the reduced surface contact area, and/or reduced mechanical advantage, specific to these features. For example, in a self-tapping design, there is a single ring or collar, within the plate hole that serves as the thread to be tapped by the threads of the screw head. This collar is also designed to be made of an alloy that is weaker than the alloy of the screw, thereby allowing one to tap the other. Inherently, this design cannot be as strong as one in which there are machined threads, providing orders of significantly more surface contact area, and where both screw and plate materials are equally strong, as opposed to mating a weaker material to a stronger material.

The preferred inventions described herein provide an approach for accommodating variable angle locking of a bone screw to an orthopedic plate without necessarily utilizing dissimilar materials, wherein one is weaker than the other.

The preferred variable angle locking design of the present invention enables an orthopedic bone fixation plate to allow a screw to be placed into the bone at various angles, both offset to the plate hole central axis and at radial orientations about the hole circumference, with the same mechanical interface and, therefore, strength, as is found with a fixed angle locking design. That is, with machined threads in the plate that mate with the machined threads on the head of the screw. Mating of machined screw threads on the head of the screw and in the plate is preferred for rigid screw/plate fixation. The preferred invention disclosed herein combines the strength and rigidity of a machined threaded interface between the bone plate and the bone screw, with the capability to position the screw in the bone at angles offset to the plate hole axis and orientations about the circumference of the hole.

BRIEF SUMMARY OF THE INVENTION

Briefly stated, one aspect of the preferred invention is directed to an orthopedic bone fixation assembly for connecting to a bone or bone fragments of a patient. The orthopedic bone fixation assembly comprises a fixation plate having a hole therein, the fixation plate including an upper surface and an opposing lower surface for positioning proximate at least one of the bone and bone fragments. A shoulder is recessed from the upper surface and an aperture extends therethrough in a direction from the upper surface to the lower surface. An insert is removably securable to the hole, the insert including a base portion and a flange extending laterally outwardly from an upper end of the base portion, and the insert defining an insert central axis extending in a direction generally perpendicular to the flange. A screw is removably securable to the insert, the screw having a screw head. The base portion of the insert has an insert hole extending therethrough with machined internal threads for threadingly engaging the screw. The insert hole defines an insert hole central axis extending in a direction offset by an offset angle relative to the insert central axis such that threaded engagement between the screw and the insert hole offsets a longitudinal axis of the screw from the insert central axis by the offset angle. The aperture of the fixation plate is dimensioned to complementarily, removably receive the base portion of the insert and the recessed shoulder is dimensioned to complementarily, removably receive the flange of the insert. The insert is configured for engagement with the fixation plate in a plurality of rotational orientations about the insert central axis to selectively orient the direction of the insert hole central axis. Subsequent threading of the screw with the insert, through the fixation plate and into at least one of the bone and bone fragments secures the assembly to at least one of the bone and bone fragments and orients the longitudinal axis screw into the underlying at least one of the bone and bone fragments along the insert hole central axis.

According to another aspect of the preferred invention, an insert that mates with the bone plate to provide a rigid interface between the plate and the bone screw. The insert includes a central hole angled at a fixed offset from an axis perpendicular (normal) to the insert top surface and machined, or tapped, to include screw threads. The central hole is of a radius and thread dimension to allow a correspondingly threaded bone screw head to screw into the insert, thereby creating a rigid fixed screw/insert interface. The insert can be fixed to the plate at a plurality of radial orientations about the central axis of the plate hole. This feature allows the bone screw to be placed into the bone at an exact orientation that can be defined by two vectors, the first referenced to the central axis of the plate hole perpendicular to the plate surface, and the other directionally radial to the hole around the circumference.

In another aspect of the preferred invention, the insert locks to the plate at any one of a plurality of radial directions around the circumference of the plate hole. The base of the insert extends into the plate hole and is threaded on the inside wall of the central opening to accept the bone screw. The exterior of the base includes locking features that interact with the plate hole. The locking features can be of any form that will provide both a rigid fixation interface with the plate and also allow the insert to be positioned at a variety of radial directions around the circumference of the hole. In one preferred embodiment, the locking feature is a small cubic tab extending from the exterior of the base portion of the insert, directed radially away from the center of the opening. There may be one or a plurality of locking tabs around the perimeter of the exterior of the base, distributed at set angles from each other. In one preferred embodiment, there are twelve locking tabs set thirty degrees (30°) apart around the perimeter of the base exterior. Insertion grooves corresponding to the insert tabs are preferably positioned in the wall of the plate hole, extending into the hole from the top surface and parallel to its central axis. The grooves are dimensioned to allow passage of the locking tabs along a path parallel to the central axis of the plate hole. Thus the insert can be placed within the plate hole by aligning the tabs with the insertion grooves and sliding the insert downward into the hole from the plate surface. The insert preferably has a flange extending radially beyond the base portion diameter and the plate preferably includes a corresponding shoulder recessed below the plate surface. The insert flange preferably stops on the plate shoulder when the insert is fully inserted into the plate hole to properly locate the insert in the plate and provide additional mechanical stability to the insert/plate interface.

In another aspect of the preferred invention, the interface between the insert and the plate includes a means for securing the insert to the plate. In one preferred embodiment, a locking groove substantially parallel to and located at some distance beneath, the plate surface intersects with the insertion groove previously described. Each insertion groove preferably has a corresponding horizontal locking groove. Thus, the insert is placed into the plate hole by aligning and sliding the locking tabs into the plate hole grooves. The insert is translated downward into the plate hole until the flange contacts the plate hole shoulder and is fully seated. The insert is then rotated about the central axis of the plate hole, translating the insert locking tabs along a path parallel to the plate surface and within the horizontal locking grooves of the plate hole wall. When the locking tabs contact the end of the horizontal locking groove, the insert becomes fully secured to the plate. Additional preferred embodiments may include other locking means to releasably secure the insert to the plate. The preferred locking tabs may be shaped with an alternate geometry, e.g., parallelepiped, to increase the frictional contact between the tab and locking groove, the locking groove may be placed at a slight angle from parallel to the plate surface simulating the security of a screw thread, the contact surface between the tab and groove may be roughened or contain features, e.g., ratchet teeth, to increase friction and therefore the strength of the interface, or other designs that provide a secure locking interaction between the plate and insert.

In another aspect of the invention, the base of the insert includes expansion relief grooves cut radially through the width of the base. The expansion relief grooves are distributed around the insert base at set angles from each other, interspersed between the insert locking tabs. In one embodiment, there are twelve locking tabs set thirty degrees apart around the perimeter of the base exterior and six expansion relief grooves oriented such that there is an equal separation between locking tabs adjacent to each relief groove. The expansion relief grooves are designed to allow for slight expansion of the insert base upon full insertion of a screw into the insert. This can be accomplished with the appropriate tapering of the screw head, insert hole, screw thread height, insert thread depth, or any combination. The expansion of the insert base via the relief grooves causes a slight radial translation of the locking tabs toward the wall of the plate hole within the horizontal locking groove. This translation would cause a sufficient amount of surface contact and opposing radial force between the locking tabs and the vertical wall of the horizontal locking groove. This frictional interaction provides additional strength to the security of the interface between the insert and the plate, thereby contributing to the rigidity of the overall construct.

In an additional aspect of the preferred invention, a drill guide is included as a tool to facilitate the insertion and locking of the insert to the plate. The drill guide is preferred in situations where a bone screw is being inserted in a bone through a plate. Coordinating the direction of the screw and proper centering of the screw hole with respect to the plate hole preferred for successful bone screw placement within a plate. In plates that include fixed angle locking, it is preferred to accomplish proper alignment of the drill guide with the axis of the thread path in the hole prior to drilling the bone in preparation for receiving the screw. Certain designs may include threads on the tip of the guide that are received into the threads of the plate hole, thereby aligning the guide in the orientation of the screw hole that allows the screw to be threaded into the plate. In a preferred embodiment of the invention, the drill guide includes connecting members that extend from the distal end of the guide. The connecting members interface with the flange of the insert in a manner that removably secures the insert to the drill guide.

The insert could be designed as a feature of the drill guide such that the guide is manufactured with the insert removably attached. The drill guide and insert may also be provided as separate components and attached prior to or during the surgical procedure. In this case, the drill guide design would advantageously allow connection to all inserts regardless of the angulation offset of the screw hole relative to the insert central axis. Because the drill guide cannula is preferably accurately aligned with the screw hole, placement of the drill guide onto the insert would thereby include sufficient adaptability of the interface between the connecting feature of the guide and the receiving feature of the insert such as to allow for proper alignment.

According to another aspect, the invention includes a ring-shaped component with one or more wedge-shaped members, or fingers, extending in the same direction substantially orthogonal to the plane of the ring and distributed around its circumference. These fingers are designed with the intent to be inserted into corresponding slots in the interior surface of the screw hole in the bone plate. The slots in the screw hole are of similar dimension to the fingers, with the exception that the radial depth of the slots is slightly less that the radial depth of the fingers. In this arrangement, as the fingers are partially inserted into the slots in the screw hole, the interior diameter, and therefore the radial continuity of the interior surface, of the hole is unchanged in terms of surface contact with a screw head that may be placed within the screw hole. However, once the fingers are completely inserted into the slots, the wedge-shape due to the radial differences translates the interior surface of the fingers slightly above the interior surface of the screw hole. This reduction in diameter of the interior of the screw hole relative to a bone screw head diameter causes inward radial force to be applied from the interior wall of the screw hole slot, through the fingers, onto the head of the bone screw. The inward radial force, in turn, is demonstrated as a frictional "crush lock" which acts on the bone screw head to fix it in its orientation at the time of locking. The combination of the fingers and support ring are therefore henceforth referred to as the compression lock mechanism.

In another aspect of the invention, a securing cap similar in size to the compression lock mechanism support ring can be inserted after insertion of the locking component into the screw hole. The securing ring has external threads which thread into threads of the screw hole. As the securing ring is threaded into the screw hole, it forces the compression lock mechanism down into the screw hole thereby forcing the locking fingers into the hole slots and causing them to impinge radially on the screw head and lock it in its angular position. The securing ring maintains its position against the locking component thereby keeping the screw locked at the desired angle until the securing ring is removed by unscrewing it from the screw hole threads.

In another embodiment of the invention, the compression lock mechanism has a plurality of finger projections distributed around the circumference of the locking ring. Similarly, the corresponding slots in the interior of the screw hole are distributed around the circumference of the screw hole. In this embodiment, three or more of the locking fingers, when completely inserted into the slots, will impart internal force against the screw head in a circumferential distribution around the head. In this configuration, the entire frictional force imparted on the screw head would be due to the inward force of the locking fingers.

In another embodiment of the invention, the ring-shaped component has one or more finger projections arranged within one half of the circumference of the locking ring. The corresponding slots in the interior of the screw hole are arranged in the same way so that the fingers are aligned with the slots when the locking ring component is placed into the screw hole. In this embodiment, when the locking fingers are completely inserted into the slots, the locking fingers will impart an internal force against the screw head along only one half of the head circumference. In this configuration, the frictional force imparted by the fingers onto the screw head will impinge the screw head between the fingers and the opposite wall of the screw hole, thereby locking the screw in the desired angle relative to the axis of the screw hole.

In another embodiment of the invention, the leftmost edge of the slot in the plate hole is tapered or chamfered to entice the finger of the compression locking mechanism to seat into the slot as the screw is being inserted into the bone. If the compression locking mechanism is inserted into the plate hole prior to the screw being inserted, or if the compression locking mechanism is attached to the screw head prior to the screw being inserted, it will be convenient for the fingers of the compression locking mechanism to self-seat into the hole slots as they are frictionally turned with the screw in a clockwise manner in the hole during screw insertion. Once the fingers are seated into the slots, the frictional force of rotation imparted by the screw head will be overcome and the compression locking mechanism will remain aligned with the hole slots.

In another embodiment of the invention, the circumferential surface of the slots and the corresponding outer circumferential surface of the compression locking mechanism fingers include features that provide a one-way lock, such that the translation of the finger into the slot cannot be reversed thereby eliminating the need for a securing cap. The one-way features could include a toothed ratchet design, roughened surface, or other similar features providing the desired function. The downward force needed to fully insert the compression locking mechanism into the slots could be caused by the friction of the screw head against the finger surface or by an external mechanical means, such as a tool, forcibly acting on the compression locking mechanism ring.

According to another aspect, the invention described herein includes a rotatable insert and bushing that mate with the bone plate to provide a rigid interface between the plate and the bone screw. The insert includes a central hole within which screw threads are machined, or tapped, at an angle normal (i.e., perpendicular) to the top surface of the insert. The central hole is of a radius and thread dimension to allow a correspondingly threaded bone screw head to screw into the insert, thereby creating a rigid fixed screw/insert interface. The insert is positioned within the bushing, the latter component allowing the insert to rotate about an axis through the center of the central hole and parallel to the bushing top surface. The bushing, in turn, is positioned within the plate hole and is rotatable about an axis through the center of the hole and perpendicular to the plate surface. These features allow the bone screw to be placed into the bone at an exact orientation that can be defined by two vectors, the first referenced to the central axis of the plate hole perpendicular to the plate surface, and the other directionally radial to the hole around the circumference.

The insert is sectioned into halves such that there is a small gap created along a plane cutting centrally through the threaded hole and intersecting the hole axis. The insert sections are provided the freedom to travel linearly toward and away from each other within the bushing, while simultaneously being allowed rotational freedom within the bushing about an axis through the center of the hole and parallel to the plate surface. The insert assembly and bushing together are also allowed rotational freedom within the plate hole about an axis perpendicular to the plate surface. The outer circumference of the insert is provided with features that engage and lock onto the inner surface of the bushing when the insert sections are linearly separated from each other, i.e., the gap between the insert sections is at a distance such that the insert threaded hole at its original radius. With the insert gap reduced, the engagement features on the insert are distanced from the bushing inner surface and the insert assembly is therefore free to rotate about the previously described axis or rotation. When a screw, or other cylindrical object of equal diameter, is placed within the hole, the insert sections are again separated and the engagement features engage with the inner surface of the bushing, thereby preventing the insert from further rotation relative to the bushing. The bone screw is subsequently locked at an angle relative to the plate surface through the mechanical interfaces of the insert, bushing, and plate hole.

Beyond the radial distance of engagement features from the insert hole center is an additional feature of the insert that engages with the inner surface of the plate hole. The bushing, at the location of the additional insert feature, contains a window through which the additional insert engagement feature can be translated. Thus, when the insert sections are separated, the additional insert feature is extended through the bushing window and comes into engagement with the inner aspect of the plate hole. In this configuration, the insert, as described above, is engaged and rotationally locked to the bushing, however the bushing, if without this feature, would remain free to rotate about its central axis relative to the plate. With the additional insert feature extended beyond the bushing and engaged with the inner aspect of the plate hole, the construct of the insert and bushing is thereby also prevented from rotation about the central axis of the bushing.

In a procedure in which such an insert, bushing, plate construct is used, the orthopedic plate is positioned on a bone at a location conducive to effecting the desired fixation. The insert in the hole chosen for a variable angle locking screw is held such that the gap between the insert sections was sufficiently reduced to prevent the insert engagement features from engaging with either the bushing or plate. The insert is then oriented in a direction radial to the perpendicular axis of the plate hole. This direction is that of the desired placement of the screw if the screw were to be angled relative to the perpendicular axis of the plate hole. With the radial direction set, the insert is rotated about its axis parallel to the plate surface. This direction is that of the desired angle of the screw relative to the plate surface. With both the radial direction and angular offset relative to the plate surface set, the insert is then held such that the gap between the insert sections is at its original length. With the insert sections separated, the insert engagement features engage with the bushing and plate thereby locking the insert in both radial direction and angular offset. A hole is then drilled into the bone along the central axis of the threaded insert hole. The screw is then inserted into the bone until the screw head begins to enter into the insert, then the threaded screw head is inserted into the threaded insert hole. With the screw head fully inserted into the threaded insert, the insert sections and engagement features are further pressed against both the bushing and plate and the entire construct becomes rigidly locked in place along every degree of freedom.

BRIEF DESCRIPTION OF THE SEVERAL VIEWS OF THE DRAWINGS

The foregoing summary, as well as the following detailed description of the disclosure, will be better understood when read in conjunction with the appended drawings. For the purpose of illustrating the disclosure, there is shown in the drawings preferred embodiments of an orthopedic implant which are presently preferred. It should be understood, however, that the disclosure is not limited to the precise arrangements and instrumentalities shown. In the drawings:

FIG. 9 is an isometric view of a bone fixation plate screw hole showing the compression locking mechanism slot features described herein;

FIG. 10 is a view of a compression lock mechanism with three locking fingers;

FIG. 11A is a section view of a bone fixation plate hole showing the profile of one of the compression locking mechanism finger slots. The inner and outer walls of the slot have radii that are both different in length and center position. These differences provide a wedge-shaped profile along the curved portion of the slot;

FIG. 11B is a graphic of the geometric dimensions that are used to calculate the extent and position of the bone fixation plate slot and the compression locking mechanism finger wedge-shaped profiles;

FIG. 12 is a side view of the compression locking mechanism showing the profile of one of the wedge-shaped locking fingers. The inner and outer walls of the fingers have radii that are both different in length and center position. These differences provide a wedge-shaped profile along the curved portion of the fingers;

FIG. 13A is a side view of a locking finger partially inserted into a finger slot such that the thickness of the finger and the depth of the slot are equivalent. The inner surface of the finger, therefore, is continuous with the surface of the hole;

FIG. 13B is a side view of a locking finger fully inserted into a finger slot such that the thickness of finger exceeds the depth of the slot. The inner surface of the finger, therefore, is raised above the surface of the hole;

FIG. 14 is a view of the compression lock mechanism in position around the head of a non-locking, i.e., the head has no threads, bone screw;

FIG. 15A is a view of the locking cap in position when locked against the compression locking mechanism. The bone fixation plate is purposefully absent for visibility;

FIG. 15B is an isometric view of a bone fixation plate screw hole with the compression locking mechanism in the fully inserted position, with the bone screw purposefully absent for visibility;

FIG. 16A is a view of the bone screw with the compression locking mechanism in position on the screw head, being placed into the bone fixation plate hole;

FIG. 16B is a view of the bone screw and compression locking mechanism inserted into the bone fixation plate hole. The locking cap is positioned above the plate hole and in position to be inserted;

FIG. 16C is a view of the bone screw in the bone fixation plate hole, with the locking cap fully inserted and bone screw locked in its final angular position relative to the fixation plate;

FIG. 17 is a view of the compression locking ring and the bone plate hole slots both having corresponding one-way ratcheting teeth that engage with one another as the fingers are translated into the slots;

FIG. 18 is an isometric top view of a first insert section, showing bushing and plate engagement features;

FIG. 19 is an isometric top view of a second insert section, complementary to that of FIG. 18;

FIG. 25A is a sectioned side view of a bushing and two insert sections. The insert sections are positioned with the gap reduced and the first and second insert sections in contact thereby allowing rotation relative to the bushing about an axis perpendicular to the page. The insert is at a rotational position whereby the central axis of the threaded hole is perpendicular to the top surface of the bushing;

FIG. 25B is a sectioned side view of a bushing and first and second insert sections. The first and second insert sections are positioned with the gap expanded such that the threaded hole is at its original diameter, with the first and second insert engagement features engaged with those of the bushing. The insert is at a rotational position whereby the central axis of the threaded hole is perpendicular to the top surface of the bushing;

FIG. 25C is a sectioned side view of a bushing and first and second insert sections. The first and second insert sections are positioned with the gap expanded such that the threaded hole is at its original diameter, with the first and second insert engagement features engaged with those of the bushing. The insert is at a rotational position whereby the central axis of the threaded hole is angled 10 degrees relative to the top surface of the bushing;

FIG. 26A is an isometric side view of the screw locking assembly with a screw inserted into the threaded insert assembly hole. The screw is shown in a locked position at an angle of zero degrees relative to the top surface of the plate;

FIG. 26B is an isometric side view of the screw locking assembly with a screw inserted into the threaded insert assembly hole. The screw is shown in a locked position at an angle of fifteen degrees relative to the top surface of the plate and at a radial direction along a plane parallel to the page.

DETAILED DESCRIPTION OF THE INVENTION

Figure 1:
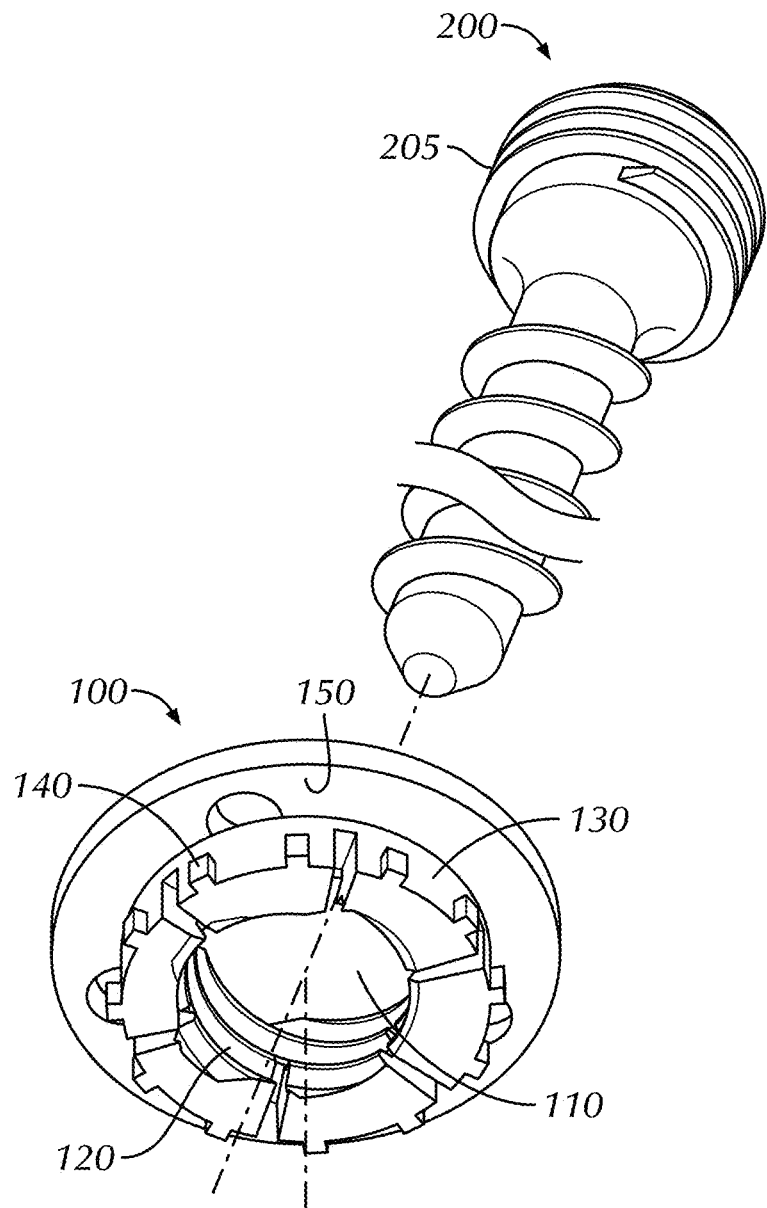
FIG. 1 is an exploded, isometric bottom view of a fixation plate insert for a preferred variable angle bone screw locking plate, showing the base portion with screw threads, locking tab, and relief groove features, and a bone screw for threading to the insert.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the orthopedic implant, and designated parts thereof, in accordance with the present disclosure. Unless specifically set forth herein, the terms "a," "an" and "the" are not limited to one element, but instead should be read as meaning "at least one." The words "inwardly" or "distally" and "outwardly" or "proximally" refer to directions toward and away from, respectively, the patient's body, or the geometric center of the preferred plate, insert or instrument and related parts thereof. The words, "anterior", "posterior", "superior," "inferior", "lateral" and related words and/or phrases designate preferred positions, directions and/or orientations in the human body to which reference is made and are not meant to be limiting. The terminology includes the words noted above, derivatives thereof and words of similar import.

It should also be noted that the terms "first," "second," "third" and the like may be used herein to modify various elements. These modifiers do not imply a spatial, sequential, or hierarchical order to the modified elements unless specifically stated. It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-8 a preferred insert 100 for receiving and securing a preferred orthopedic bone screw 200 to a preferred bone fixation plate 300. The insert 100 includes a screw hole 110 and threads 120 for receiving the threaded head 205 of the bone screw 200. The screw threads 120 of the screw hole 110 are preferably formed by machining into the inner surface of a base portion 130 of the insert 100. The base portion 130 extends to or has a depth such that a sufficient number of threads 120 can be machined into the inner surface to allow for insertion and rigid fixation of the screw head 205, appropriate for the strength requirements of orthopedic surgery. A plurality of locking tab features 140 is preferably located on the outer surface of the base portion 130. A flange 150 preferably extends radially from the top portion of the insert 100 and provides a contact surface for aiding in securing the insert 100 to the bone fixation plate 300.

Figure 2:
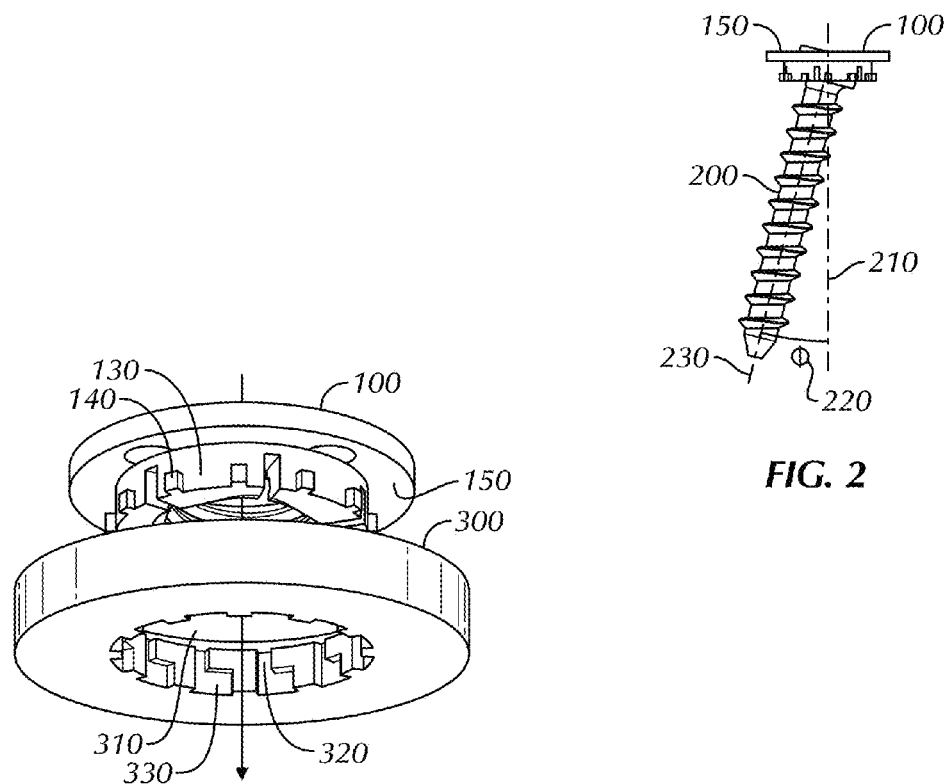
FIG. 2 is a side view perspective of a bone screw fully threaded into a preferred insert, the insert designed with an offset angle of Φ degrees from the central axis.

The screw hole 110 direction is preferably offset with respect to the surface of the flange 150, as shown in FIG. 2, such that once the screw 200 is threaded into the insert 100 it is held at an angle phi (Φ) 220, which may take-on various magnitudes, such as zero degrees (0°) to thirty degrees (30°). A central axis 210 of the insert 100 is defined as being perpendicular to the top surface of the flange 150 and the central axis 210 is also preferably and typically substantially perpendicular to a top surface of the plate 300. A thread axis 230 of the insert hole 110, i.e., the central axis of the insert hole 110, and, therefore, the longitudinal axis of the screw 200 when the screw 200 is secured to the insert 100 are then directed at an offset angle Φ or 220 relative to the central axis 210 of the hole 110. The offset angle Φ can be any angle greater than or equal to zero degrees (0°), with a preferred range from zero to twenty five degrees (0-25°), but not limiting. In one preferred embodiment, the insert 100 has a singular offset angle 220 and will retain and secure a bone screw 200 at that angle relative to the insert 100 and, subsequently, the plate 300, when the insert 100 is secured to the plate 300.

A combination of alternative variable angle locking means, including but not limited to cross-threading, tapping, and crush-locking features, may be combined with the preferred present invention of the combined screw 200, insert 100 and plate 300, to provide for slight variability of the screw angle relative to the singular offset angle 220. The addition of alternative variable angle locking means to the present preferred invention offers additional flexibility to a surgeon for placement of the screw 200 into the bone, and may be provided in a manner that limits the range of angular displacement compared to typical constructs, but with an increase in rigidity of the plate 300 to screw 200 interface.

Figure 3A:
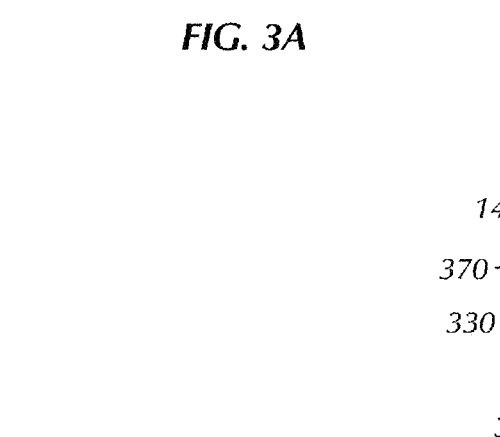
FIG. 3A is an isometric bottom view of the preferred insert and portion of a plate hole with portions of the plate excluded for clarity, wherein the locking tabs on the insert are shown in alignment with the grooves in the plate hole walls.
Figure 3B:
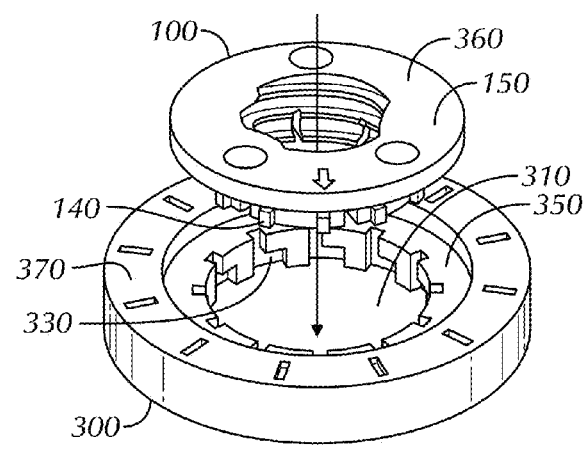
FIG. 3B is an isometric top view of the preferred insert and a portion of a plate hole with portions of the plate excluded for clarity, wherein the locking tabs on the insert are shown in alignment with the grooves in the plate hole walls.

Referring to FIGS. 3A and 3B, the insert 100 is preferably placed into and secured to the bone fixation plate 300 during use. For the purposes of clarity, the plate 300 is depicted as a circular section, but it should be understood that the bone fixation plate 300 described herein is intended to be geometrically similar to other orthopedic plates known in the art and portions of the plate 300 are excluded for clarity. A hole 310 in the bone fixation plate 300 is adapted to receive the insert base portion 130. The inner surface of the fixation plate 300, defining the hole 310, preferably contains a plurality of insertion grooves 320, dimensioned to receive the insert locking tabs 140. In the preferred embodiment, the insertion grooves 320 have walls that are orthogonal, aligned with the central axis of the insert hole 210 and parallel to the plate hole 310 surface. Other groove shapes, however, e.g., hemi-cylindrical, triangular, etc., as well as other alignments, e.g., angularly offset from the central axis 210, helical, etc. are also contemplated as features capable of serving the same function. A recessed shoulder 350 in the plate top surface 370 preferably surrounds the hole 310. The recessed shoulder 350 is dimensioned to receive the insert flange 150. In the preferred embodiment, when the insert 100 is fully inserted into the plate hole 310, the top surface of the insert flange 360 is substantially in the same plane as, e.g., flush with, the surrounding top surface 370 of the fixation plate 300. It is contemplated, however, that when fully inserted, the top surface of the insert flange 360 could also be above or below the top surface 370.

Locking grooves 330 are preferably located at or near the bottom portion of the fixation plate hole 310 and are preferably dimensioned to receive the insert locking tabs 140. In the preferred embodiment, the locking grooves 330 intersect with the insertion grooves 320 and the general direction of the locking grooves 330 is substantially perpendicular to the insertion grooves 320, but are not so limited. It is contemplated, however, that the direction of the locking groove 330 could be as a simple extension of the insertion groove 320, i.e., a continuation along the same path of the insertion groove 320, be a curved progression extending from the end of the insertion groove 320, or intersect the insertion groove 320 at an angle different from perpendicular, i.e., ninety degrees (90°). In the preferred embodiment, the locking grooves 330 have walls that are similar in geometry to the insertion grooves 320, however other groove shapes, e.g., hemi-cylindrical, triangular, etc., are also contemplated as capable of serving the same function. The entrance of the locking grooves 330 may also include a feature that encourages one-way translation of the locking tabs 140 into the locking grooves 330. This may be an offset, i.e., a step, in the depth of the locking grooves 330 relative to the depth of the insertion grooves 320, i.e. radially from the hole central axis 210, a ramp similar to a ratchet tooth, a buttress, roughened surface, or other similar mechanical feature known in the art for limiting travel of one component relative to another. In the preferred embodiment, the locking grooves 330 are in a substantially bayonet-like locking configuration.

In the preferred embodiment, the point at which the locking grooves 330 intersect the insertion grooves 320 is the equivalent distance below the recessed shoulder 350 of the fixation plate 300 as the locking tabs 140 are below the bottom surface of the flange 150. Thus, when the insert 100 is fully seated in the fixation plate 300, the insert locking tab 140 is at the intersection of the insertion groove 320 and the locking grooves 330 and is aligned so as to enable entrance into the locking grooves 330. In alternative preferred embodiments, however, the locking tabs 140 and, therefore, the insert 100 as a whole, may translate further into the plate hole 310 when the locking tabs 140 are at the intersection of the insertion grooves 320 and the locking grooves 330, given locking grooves 330 that are not directed substantially parallel to the plate surface 370. Thus, the point at which the locking grooves 330 intersect the insertion grooves 320 is a lesser distance below the recessed shoulder 350 of the fixation plate 300 as the locking tabs 140 are below the bottom surface of the flange 150.

Figure 4A:
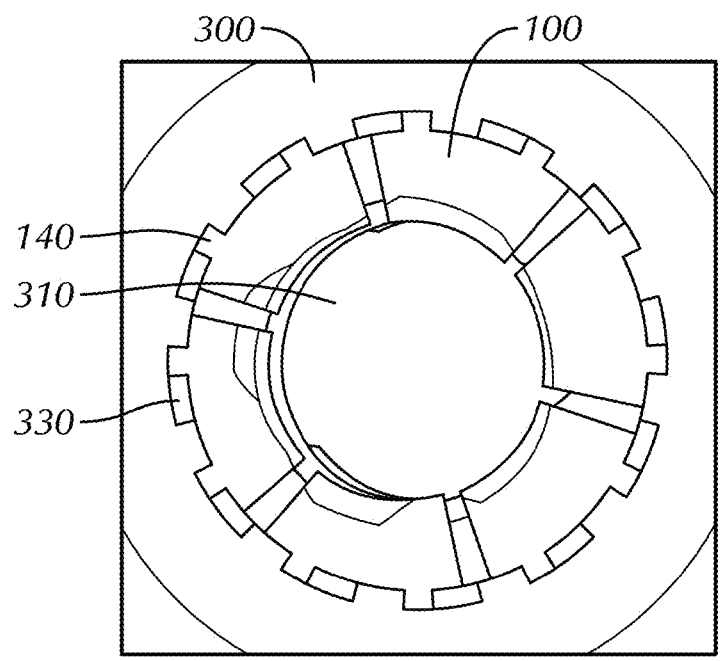
FIG. 4A is a bottom view of a preferred fixation plate with a preferred insert fully inserted, but not locked, in the plate hole.
Figure 4B:
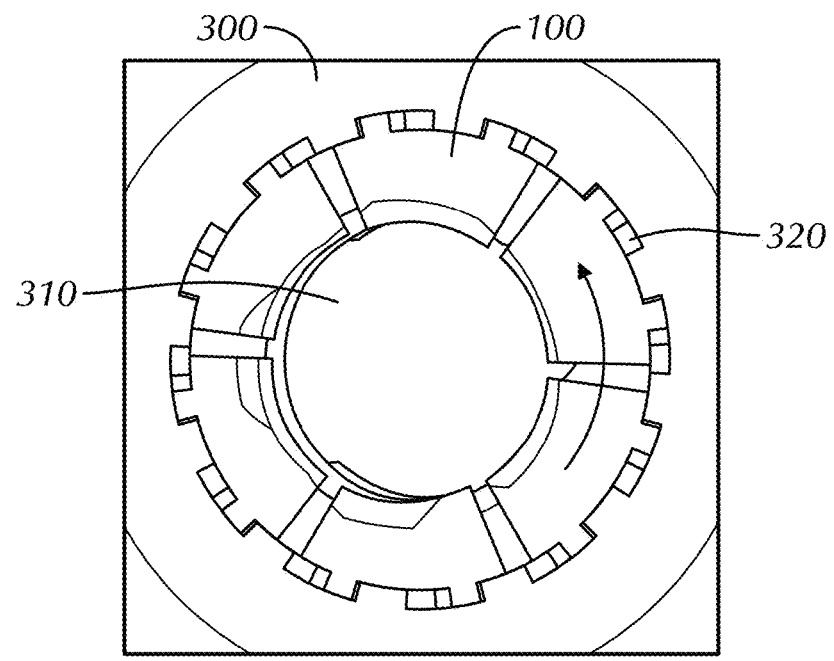
FIG. 4B is a bottom view of a preferred fixation plate with the preferred insert fully inserted and locked in the plate hole.

A length of the locking grooves 330, i.e., the distance along the circumference of the inner wall of the plate hole 310 defining the hole 310, is preferably limited such that the locking grooves 330 do not intersect two neighboring insertion grooves 320. In this way, when the locking tabs 140 are translated into and along the locking grooves 330, their travel is limited by the length of the locking grooves 330 and prevented from entering a neighboring insertion groove 320. As shown in FIGS. 4A and 4B, when the locking tabs 140 reach the intersection of the insertion grooves 320 and the locking grooves 330, the insert 100 is removable from the fixation plate hole 310 by reversing the direction of insertion. If the insert 100 is rotated about the central axis 210 in a counter-clockwise direction, as viewed in FIG. 4B from the fixation plate bottom, the locking tabs 140 enter the locking grooves 330 and, upon continued rotation, abut the end of the locking grooves 330 and thereby are prevented from further counter-clockwise rotation. In this position, the locking tabs 140 are no longer aligned with the insertion grooves 320. Thus, the insert 100 generally cannot be further translated along the central hole axis 230 in either direction nor can it be further rotated in a counter-clockwise direction. Alternative preferred embodiments of the insertion and locking grooves 320, 330, as indicated above, would provide a configuration for a similarly locked construct.

Figure 5A:
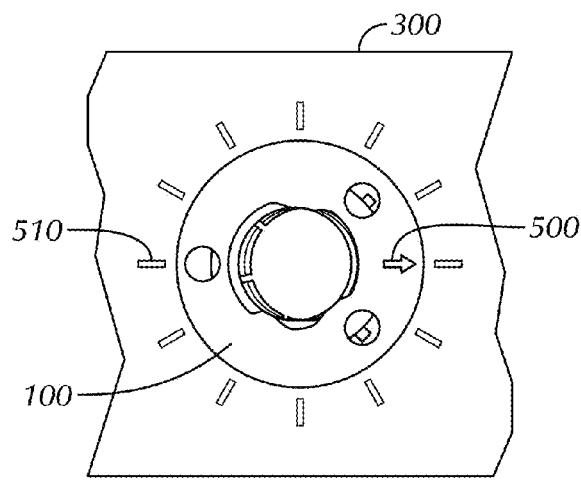
FIG. 5A is a top plan view of a preferred bone fixation plate with an insert secured in a plate hole, showing alignment markings on the insert indicating the direction of the screw angulation, and corresponding marks on the plate indicating the plurality of possible orientations available for the insert.
Figure 5C:
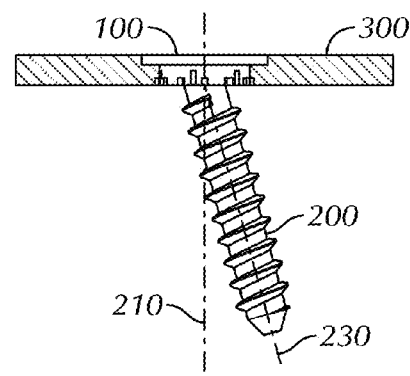
FIG. 5C is a side cross-sectional view of a preferred bone fixation plate with an insert and a screw mounted thereto, with the screw shown at an angle offset from the central axis of the insert and offset from a perpendicular to the plate surface.
Figure 5B:
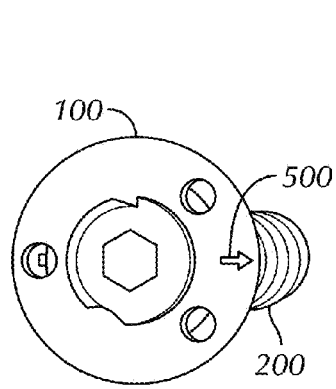
FIG. 5B is a top plan view of a preferred bone screw fully threaded into a preferred insert with the screw at an angle offset from the insert central axis.

Referring to FIGS. 1-3B, the features of the insert 100 and the bone fixation plate hole 310 provide for a method of rigidly locking a bone screw 200 at a variety of orientations to a bone fixation plate 300. The surgical procedure for securing two segments of a bone (not shown) with a preferred embodiment of the invention disclosed herein would follow a sequence similar to that described below. Referring to FIGS. 1-8, the bone fixation plate 300 is placed on the bone at a location and position advantageous for stabilizing the bone segments, fragments or portions. The insert 100 is aligned with the plate hole 310 in such a way that the insert locking tabs 140 are aligned with the plate insertion grooves 320. As shown in FIG. 3B, a plurality of insertion grooves 320 in equal number and spacing to the insert locking tabs 140 provide for a multiplicity of orientations in which the insert 100 can be oriented relative to the fixation plate 300. As shown in FIG. 5A, the plate top surface 370 may include markings 510, coordinated with the insertion grooves 320, to indicate the specific direction options for orienting the insert 100. Correspondingly, a marking 500 on the insert 100 may be included to indicate the direction of the insert thread hole axis 230 and therefore the bone screw 200, as shown in FIG. 5B. The insert 100 is, therefore, first oriented in the direction that will result in the desired placement of the bone screw 200 into the bone, and then the locking tabs 140 are aligned with the closest insertion grooves 320. The insert 100 is then translated downward into the fixation plate hole 310 with the locking tabs 140 translating downward within the insertion grooves 320. The insert 100 is stopped at the point when the flange 150 comes into contact with the plate recessed shoulder 350 and the locking tabs 140 are at the entrance of the locking grooves 330. The insert 100 is then preferably rotated in a clockwise fashion, as viewed looking down at the top of the plate 300, and the locking tabs 140 are translated into the locking grooves 330 until the rotation is stopped when the locking tabs 140 come into contact with ends of the locking grooves 330. A preferred drill guide 700 is then affixed to the insert 100, typically threaded into the insert 100 for proper alignment, and the bone is drilled with an appropriately sized drill bit (not shown). The drill bit and guide 700 are removed and a screw 200 is inserted into the insert hole 110. As the screw 200 is driven into the bone, the screw head 205 will eventually enter the insert hole and the screw head 205 will be threaded into the threads 120 of the insert 100. The clockwise rotational force used to insert the bone screw 200 will be partially translated to the insert 100 via friction, however the insert 100 is generally prevented from further clockwise rotation because of the position of the locking tabs 140 at the end of the locking grooves 330. Once the screw head 205 is fully threaded into the insert 100, the screw 200 is rigidly and securely locked to the fixation plate 300 in the desired orientation, shown in the section view FIG. 5C, and the bone segment into which the screw 200 was placed, is held equally securely.

Figure 6:
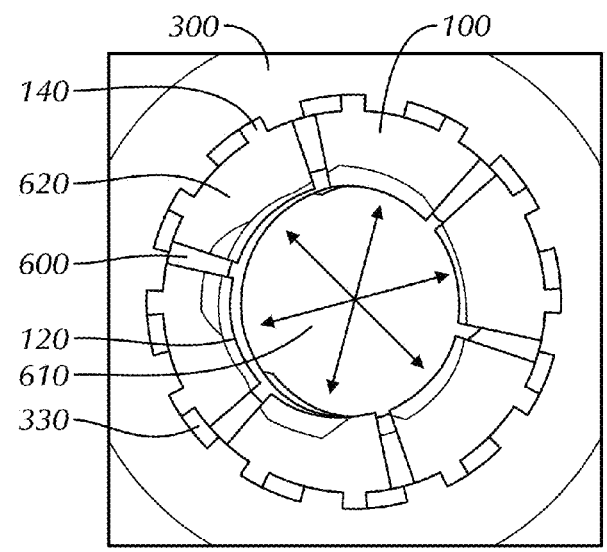
FIG. 6 is a bottom plan view of the preferred insert fully inserted and locked in the preferred bone fixation plate hole, with arrows indicating directions of radial forces imparted on the insert base by a screw head when threaded into the insert hole.
Figure 7:
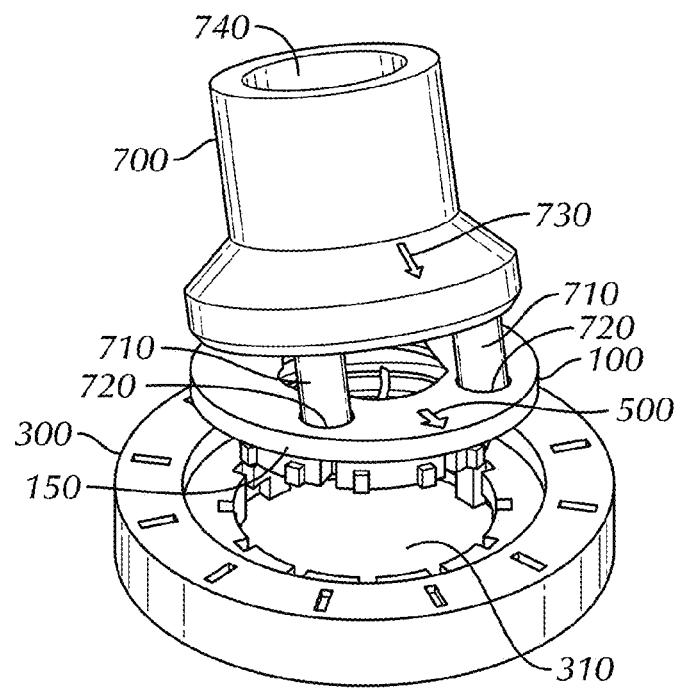
FIG. 7 is a view of a preferred bone fixation plate hole, insert, and a distal portion of a drill guide that is attached to the insert by connecting members extending from its distal end, and corresponding circular openings in the insert flange that receive the connecting members.
Figure 8:
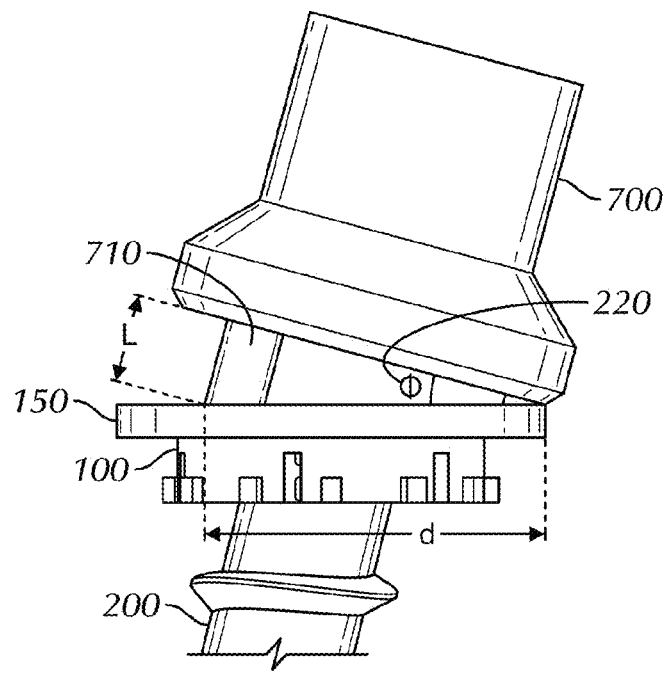
FIG. 8 is a side elevational view of a preferred insert attached to the distal portion of a preferred drill guide, showing dimensions associated with the distance "D" across the insert between the connecting members and the length "L" of a connecting member that preferably define an offset angle of the insert hole and inserted screw.

An additional mechanism to rigidly secure the insert 100 to the fixation plate 300 is shown in FIG. 6 showing a bottom view of the insert 100 in the locked position in the fixation plate 300. A plurality of expansion relief grooves 600 are placed around the circumference of the insert base 130, oriented radially from the hole central axis 210, forming an insert base sections 620. The expansion relief grooves 600 are of a quantity and dimensioned such that the insert base portion 130 remains of sufficient strength to allow both the locking tabs 140 and the hole threads 120 to function as intended, while also allowing sufficient flexibility in the insert base sections 620 to expand radially in response to an outward radial force. As described in the above method for utilizing the preferred invention, threading the bone screw head 205 into the insert hole threads 120 is the typically the final step in securing the bone screw 200 to both the bone and fixation plate 300. A preferred embodiment of the insert base 130, which includes expansion relief grooves 600, utilizes this action to increase the security and rigidity of the interface between the insert 100 and the fixation plate 300, thereby increasing the security and rigidity of the fixation of the bone screw 200 to the plate 300. The insert hole 110 includes an inward draft or taper such that the diameter of the insert hole 110 closest to the bottom of the insert base 130 is slightly smaller than the diameter of the corresponding lower portion of the screw head 205 of the screw 200. The difference in diameters between the insert hole 110 and the screw head 205 of the screw 200 may be due to differences in screw thread height, screw core diameter, hole thread depth, hole diameter, or a combination thereof.

Referring to the preferred method of utilization, when the screw head 205 of the screw 200 is fully threaded into the insert hole 100, the difference in diameters preferably results in radially outwardly directed force vectors, as depicted in FIG. 6 by arrows 610. The insert base sections 620 react to the force vectors 610 by expanding radially about the insert thread axis 230. This radial expansion is translated to the circumferential surfaces of the locking tabs 140 which are impeded from further radial translation when the tab surfaces contact the circumferential inner wall of the locking grooves 330. The surface contact between the locking tabs 140 and the locking grooves 330 create equal and opposite resultant force vectors, thereby inducing a frictional force at the surface intersection therebetween. This frictional force may be increased further with features on one or both of the contact surfaces. Such features include abrasive or roughened surfaces, malleable materials to increase surface contact area, ridges, or other means known in the art. Given sufficient expansion to overcome clearances and tolerances among the components, the resulting frictional force provides a significant increase to the rigidity of the interface between the insert 100 and the plate hole 310.

Turning back to the preferred method of utilization, the step of aligning the insert 100 with, and inserting the insert 100 into, the fixation plate 300 at the desired orientation can be facilitated by using a tool 700 to hold the insert, especially considering the size of the insert 100 and the surgical environment. The preferred drill guide 700 and insert 100 shown in FIG. 7 include features that allow the insert 100 to be removably attached to the drill guide 700. A plurality of connecting members 710 extend from the distal end of the drill guide 700. The connecting members 710 are received into corresponding recesses 720 in the insert flange 150. In this preferred embodiment, three connecting members 710 are cylindrical and dimensioned relative to the recesses 720 in the insert 100 in such a way that there is sufficient interference as to allow insertion of the cylinders 710 into the recesses 720 while also providing a frictional force that removably secures the insert 100 to the guide 700. The shown and described preferred embodiment of the drill guide 700 is not limiting and other configurations of the connecting members 710 are contemplated, e.g., square, triangular, elliptical, etc. shapes, two or more in number, or a singular extension of the guide 700. The markings 500 and 730 on the insert 100 and drill guide 700, respectively, aid in properly aligning the connecting members 710 to the recesses 720 and orienting the screw 200 to the plate 300. Additional mechanisms or features to removably secure the insert 100 to the drill guide 700 could include, but are not limited to, flexible members extending from the guide that hook under the flange, a key slot in the flange with corresponding keyed extension members to fit and secure into, a magnetic feature to maintain a sufficient connection between the insert 100 and guide 700, or other means known and understood by one skilled in the art.

The feature for removably attaching the insert 100 to the drill guide 700 does not only provide for temporary fixation of the insert 100 to the drill guide 700 but also for transferal of a rotational force, or other necessary action, imparted on the insert 100 through the drill guide 700 to lock the insert 100 to the fixation plate 300. Other mechanisms or features of locking the insert 100 to the plate 300 may include an interface that provides for force transfer along other dimensions, or manipulation of the extension members.

In the illustrated preferred embodiment of the guide 700, three cylindrical connecting members 710 extending from the distal aspect of the drill guide 700 are of varying lengths, such that, when secured to the insert 100, the arrangement of the connecting members 710 align a central cannula 740 of the guide 700 with the insert thread axis 230. For example, in the illustrated preferred embodiment, the three connecting members 710 of the drill guide 700 define unequal lengths, having two members of equal length and one substantially shorter, creating a tripod base. The length of the longer members 710 would be sufficient to accommodate alignment of the drill guide 700 with an insert 100 having potentially the largest screw offset angle 220. As an example, and shown in FIG. 8, with the short connecting member dimensioned such that the proximate drill guide end surface rests directly on the insert flange 150, the minimum length of the longer connecting members 710 are calculated by the following equation: L=D sin Φ, where D is the distance between the contact points of the extensions on the insert flange 150, L is the length of the long extension(s) and phi (Φ) is the offset angle 220 of the screw 200 relative to the central axis of the hole 110.

Because the length of the longest connecting members 710 is fixed, the recess feature 720 of the insert 100 then accommodates a residual amount of this length when the drill guide 700 is mated with an insert 100 having the smallest screw offset angle 220. In the illustrated preferred embodiment, recesses 720 that extend in part into the insert base 130 provide sufficient space to accommodate the residual connecting member length. It is contemplated that alternative accommodations in the insert flange 150, base 130, or recessed shoulder 350 of the fixation plate 300 could be made, including grooves or similar recesses appropriate for the dimensions and locations of the connecting members 710.

Turning to FIGS. 9-17, a bone fixation plate hole 1001 (FIG. 9) is described with a spherical bottom surface portion 1501 and a bottom screw hole 1401 for receiving a bone screw. Within the screw hole are slots 1101 with a surface 1701 dimensioned at a varying radial depth from the spherical bottom surface 1501 and distributed circumferentially around the center axis of the hole. The surface 1701 may be smooth, textured, or have ratchet-type features that are described in more detail below. Alternative embodiments of the slot configuration are anticipated and could include fewer or greater numbers of slots, distributed symmetrically or asymmetrically around the bottom surface 1501 as described in more detail below. A widened shelf portion 1201 of the hole located at the top of the spherical bottom surface 1501 is provided to receive the compression locking mechanism 2001, not shown in this figure. Above the hole shelf 1201 are threads 1301 cut into the plate for receiving a securing cap 6001, not shown in this figure. An alternative embodiment of the plate hole would not have a widened portion 1201, but would have a vertical wall extending from the horizontal circumference of the bottom portion hemisphere 1501 to the top plate surface 1601. In this configuration, the vertical wall would contain the securing cap threads 1301. In yet another embodiment of the plate hole would not have the thread feature 1301.

The preferred embodiment of a compression locking mechanism 2001 is shown in FIG. 10 and is the mating component for the fixation plate hole 1001. In the embodiment shown, there are three finger members 2101 extending from a ring member 2201, however alternative embodiments of fewer or greater numbers of fingers, distributed symmetrically or asymmetrically around the ring member 2201 circumference, are anticipated and described in more detail below. The number of fingers could correspond directly with the number of slots 1101 in the plate hole, or could be fewer in number, but always aligned circumferentially with the plate slots. The fingers are made of a flexible material such that reversible deflection of the end portions of the fingers from a set shape is possible. The set shape of the fingers 2101 may be straight or curved as shown in the figure. The fingers have an inner surface portion 2301 and an outer surface portion 2401 which is designed to mate with the plate hole slot surface 1701. The outer surface 2401 may be smooth, textured, or have features that provide for one-way translation into the plate slot. This surface feature is described in more detail below.

The slots 1101 in the bone fixation plate hole 1001 are dimensioned to create a wedge shaped profile between the slot surface 1701 and the hole bottom surface 1501. As shown in FIG. 11A, the radius 3001 of the hole bottom surface 1501 is centered at point 3101, whereas the radius 3201 of the slot surface 1701 is greater than radius 3001 and centered at point 3301 located above point 3101. The difference in radii 3001 and 3201 can be set to accommodate a desired thickness of the compression locking mechanism fingers 2101 such that the material characteristics of the fingers and the thickness of the fingers allow for the required elasticity. Referring to FIG. 11B, it can be seen that the distance between the center points 3101 and 3301, represented as distance "d", correlate to the shape of the wedge profile of the slot 1101. In general, a greater distance between the center points will translate the intersection of the slot surface 1701 and hole bottom surface 1501 in the positive "y" direction, away from the screw hole opening 1401 toward the plate surface 1601. A smaller distance between the center points will translate the intersection in the negative "y" direction, toward the screw hole opening 1401 and away from the plate surface 1601. More specifically, the relationship of the distance "d" between the center points 3101 and 3301 and the difference between the two radii 3001 and 3201, i.e., R1 and R2 respectively, must be within the following range:

$$d > R_2 - R_1$$

$$d < \sqrt{R_2^2 - R_1^2}$$

The fingers 2101 in the compression locking mechanism 2001 are dimensioned to create a wedge shaped profile along the portion intended to fit into the hole slot 1101 as shown in FIG. 12. Similarly to the relationship between the slot surface 1701 and the hole bottom surface 1501, the radius of the outer finger surface 2401 is greater than the radius of the finger inner surface 2301 and the corresponding radii centers are positioned substantially similarly to center points 3101 and 3301 such that the distance between them is equal to "d". The radius of the finger outer surface 2401 is equivalent to the radius 3201 of the slot surface 1701 and the corresponding centers would be coincident when the finger is fully seated into the slot. The radius of the finger inner surface 2301, however, is a small amount less than the radius 3001 of the hole bottom surface 1501. This dimensional difference results in a slightly thicker wedge-shape profile of the finger 2101 relative to the slot 1101.

As shown in FIG. 13A, when the finger 2101 is partially inserted in the slot 1101, the finger inner surface 2301 is at (as depicted in FIG. 13A) or beneath the hole bottom surface 1501. Upon continued translation of the finger 2101 into the slot 1101, the thicker wedge-shape profile of the finger positions the finger inner surface 2301 above the hole bottom surface 1501 as shown in FIG. 13B. A bone screw 6001 with a hemispherical head bottom surface 6101 dimensioned to have a radius R1, as shown in FIG. 14, would normally fit into the fixation plate hole such that with the screw fully inserted into the hole, the spherical head bottom surface is congruent with the hole bottom surface 1501. The screw head bottom surface and the hole bottom surface contact will remain congruent as the fingers of the compression locking mechanism 2001 are initially inserted into the hole slots 1101. However, as the compression locking mechanism fingers 2101 translate further down the slot, and culminating at the point of full insertion, the inner surface of the fingers 2301 will rise above the hole bottom surface 1501 and contact the screw head bottom surface 6101 exerting an inward radial force. This inward radial force creates friction at all points of contact between the finger inner surfaces and the screw head bottom surface, or if there is no corresponding finger located in the opposite hemisphere of the hole bottom surface, the inward radial force exerted by any one finger will result in an opposite reactive force exerted on the screw head by the portion of the hole bottom surface in that region. In either configuration, the summation of the inward radial forces seen by the screw head bottom surface 6101 will act as a frictional lock, commonly referred to as a crush lock, on the screw head thereby rigidly retaining the screw in the hole at the angular position it was in at the time the compression locking mechanism 2001 became fully inserted into the slot 1101.

The sequence of inserting and locking the screw 6001 into the fixation plate 1001 is depicted in FIGS. 16A-16C. The method of securing two bone segments with the fixation plate with the present invention is as follows: The fixation plate would be placed in the appropriate position on the bone, preferably bridging the gap between the bone segments. In the preferred embodiment, a hole would be drilled into the bone through the fixation plate bottom hole 1401 at the angle relative to the central axis of the plate hole that is appropriate for the placement of the bone screw. A bone screw 6001 with attached compression locking mechanism 2001 is inserted into the plate hole as shown in FIG. 16A. As the screw is driven into the bone, the screw head will enter the plate hole and the compression locking mechanism fingers will be positioned in the hole slots 1101. As the screw seats fully into the plate hole, the compression locking mechanism remains partially inserted in the slots and the screw head bottom surface 6101 is flush against the plate hole bottom surface 1501. A securing cap 8001 is then inserted into the plate hole and threaded in to the plate hole threads 1301. As the securing cap descends into the plate hole, the bottom surface of the securing cap comes into contact with the top surface of the compression locking mechanism ring member 2201, thereby forcing the fingers 2101 downward into the hole slots 1101. Once the securing cap is fully inserted, the fingers of the compression locking mechanism exert the inward radial locking force onto the screw head that rigidly maintains the screw is the desired position relative to the fixation plate.

In an alternative embodiment of the compression locking mechanism, the outer surface 2401 of the fingers and the slot surface 1701 include corresponding features 9001 as shown in FIG. 17. The features serve to provide a one-way locking mechanism that would allow the fingers 2101 to translate down the slots 1101, i.e., away from the plate surface 1601, but not allow translation in the reverse direction. The one-way features could include a toothed ratchet design, roughened surface, or other similar features providing the desired function. In this embodiment, the method of locking the angular position of the bone screw relative to the fixation plate would not require the securing cap. Referring back to FIG. 16B, when the bone screw 6001 seats fully into the plate hole, the compression locking mechanism remains partially inserted in the slots 1101 and the screw head bottom surface 6101 is flush against the plate hole bottom surface 1501. Rather than a securing cap, a tool designed for such purpose is placed on the top surface of the compression locking mechanism ring member 2201 and a downward force is applied to fully insert the fingers 2101 of the compression locking mechanism fully into the slots 1101. Because of the one-way features 9001 and the inward radial force due to the wedge-shaped profile, the fingers 2101 remain fully inserted in the slots 1101 and therefore the locking force persists. Alternatively, it is anticipated that certain designs and materials selected for the fingers 2101, slot surface 1701, and bone screw head bottom surface 6101 could provide for sufficient surface friction characteristics to forcibly translate the fingers into the slots as the screw head translates into the plate hole. Thus, when the screw head is fully seated within the plate hole, the fingers are fully inserted into the slots.

Turning to FIGS. 18-27, a mechanical assembly is described for the locking of a fixation screw to an orthopedic bone plate at variable angles relative to the plate surface and at variable radial orientations relative to the center axis of the plate hole. In the preferred embodiment, an insert having a threaded central hole is provided for securing a correspondingly threaded head of a screw. The insert is sectioned so that the insert as a whole is a combination of two independent pieces. As shown in FIG. 18, the first insert section 1002 has threads 1102 within the central hole for receiving a threaded screw head when paired with a corresponding second insert section. The outer aspect of the insert includes a feature 1202 for engaging the inner surface of a bushing which surrounds and retains the first insert section 1002. The bushing engaging feature 1202 is a flat flange extending from the body of the insert, proximate to the lower surface. Central to the width of the bushing engaging feature 1202 is a second engaging feature 1302 that extends radially beyond the rim of the flange. The feature 1302 is provided to engage with the wall surface of the plate hole within which the insert resides. The plate engaging feature 1302 is a tab, shown in FIG. 18 with a wedge profile, which is narrower in width than the bushing engaging feature 1202. Whereas the bushing engaging feature must engage with the bushing immediately surrounding the first insert section 1002 the plate engaging feature 1302 must be allowed to extend through the bushing to engage with the plate hole beyond the outer border of the bushing. It is contemplated that other means for engaging and restricting motion between the insert section and the bushing, and likewise between the insert section and the plate, would provide the same intended function as the flange and flange receiving features of the preferred embodiment. For example, a roughened or toothed surface of the bushing engaging feature 1202, with counterpart roughness or teeth on the inner aspect of the bushing, would serve to allow engagement and provide restrictive motion along any vector tangent to the engagement interface surface.

The first insert section 1002 also includes two tenon features 1402 extending opposite directions from the insert body along the plane defined by the walls of the gap section 1702. The tenon features are provided to engage with a rotational component having a corresponding mortise into which the tenon 1402 is placed in the final assembled configuration. The tenons 1402 serve both as a means to transfer rotation from the mortised rotational component about an axis parallel with the axis of the tenons, and additionally as a means for translation of the tenons, and thereby the insert, within the mortise in a direction perpendicular to the axis of the tenons. The first insert section 1002 also contains two slots 1502, each receiving a corresponding slide member extending from the second insert section. The slots 1502 are located on opposite sides of the insert body and each defines three orthogonal walls. The face of each slot wall along with the pairing of the slots is provided to restrict motion of the corresponding slide members to a single degree of freedom along a direction perpendicular to the plane defined by the walls of gap section 1702. Thus, any motion of the assembled inserts relative to each other is restricted to translation in a single direction extending along the slots 1502 perpendicular to the axis of the central threaded insert hole. It is contemplated that other means of limiting relative movement between the first and second inserts would provide the same intended function as the slide/slot combination of the preferred embodiment. For example, a cylindrical pin and hole combination would provide equally suitable motion restriction. Additionally, the mortise and tenon feature provides equivalent restriction of movement as the slide/slot combination and adds to the overall stability of the intended linear motion between the two insert sections.

As shown in FIG. 19, the second insert section 2002 has threads 2102 within the central hole for receiving a threaded screw head when paired with a corresponding first insert section. The threads, when considering the first and second insert sections together as a whole, are aligned with the threads of the first insert section 1102 to create a complete helical pathway for standard screw thread engagement. The outer aspect of the insert includes a feature 2202 for engaging the inner surface of a bushing which surrounds and retains the second insert section 2002. The bushing engaging feature 2202 is a flat flange extending from the body of the insert, proximate to the upper surface. Central to the bushing engaging feature 2202 is a second engaging feature 2302 that extends radially beyond the rim of the flange. The feature 2302 is provided to engage with the wall surface of the plate hole within which the insert resides. The plate engaging feature 2302 is a tab, shown in FIG. 19 with a wedge profile, which is narrower in width than the bushing engaging feature 2202. Whereas the bushing engaging feature must engage with the bushing immediately surrounding the second insert section 2002, the plate engaging feature 2302 must be allowed to extend through the bushing to engage with the plate hole beyond the outer border of the bushing.

The second insert section 2002 also includes two tenon features 2402 extending opposite directions from the insert body along the plane defined by the walls of the gap section 2702. The tenon features are provided to engage with a rotational component having a corresponding mortise into which the tenon 2402 is placed in the final assembled configuration. The tenons 2402 serve both as a means to transfer rotation from the mortised rotational component about an axis parallel with the axis of the tenons, and additionally as a means for translation of the tenons, and thereby the insert, within the mortise in a direction perpendicular to the axis of the tenons. The second insert section 2002 also contains two slide members 2502, extending from the gap section walls 2702 with each being received into a corresponding slot 1502 in the first insert section. The slide members 2502 are located on opposite sides of the insert body and each defines four orthogonal faces. The surface of each slide member face, along with the pairing of the slide members and mating with the slots 1502 restricts motion of the first and second inserts 1002 and 2002, respectively, to a single degree of freedom along the direction of the slide members and perpendicular to the plane defined by the walls of gap sections 1702 and 2702, respectively. Thus, any motion of the assembled inserts relative to each other is restricted to translation in a single radial direction extending from the axis of the central threaded insert hole perpendicular to the walls of the gap.

Figure 20A:
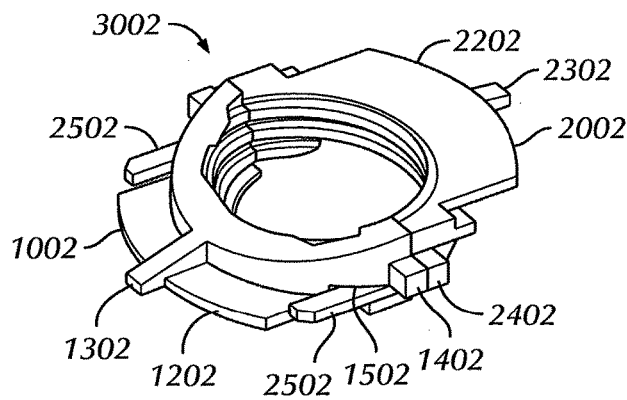
FIG. 20A is an isometric top view of the assembled first and second insert sections with the gap between the sections reduced such that the sections are in contact.
Figure 20B:
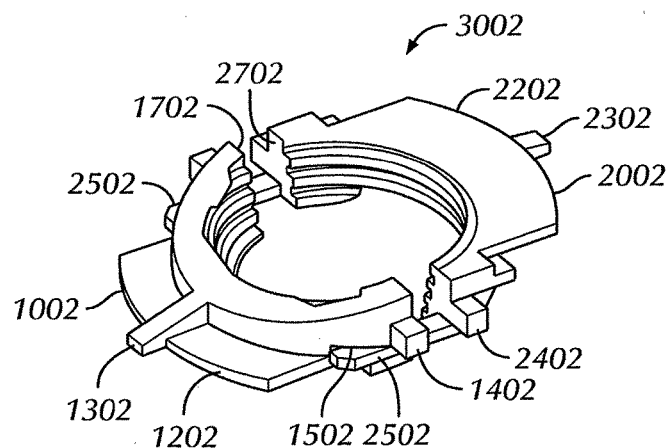
FIG. 20B is an isometric top view of the assembled first and second insert sections with the gap between the sections expanded such that the threaded hole in the insert has its original diameter.

The assembly constructed of the first insert section 1002 and the second insert section 2002 is shown in FIGS. 20A and 20B. With the slide members 2502 of the first insert section engaged within the slots 1502 of the second insert section, the insert sections are able to translate within a single degree of freedom relative to each other along an axis perpendicular to the gap section walls 1702 and 2702. Additionally, tenon features 1402 and 2402 similarly translate in accordance to their associated insert sections. FIG. 20A shows the assembly with the gap section walls 1702 and 2702 of the first insert section 1002 and second insert section 2002, respectively, in contact. This positional configuration reduces the linear distance between the radial extent of the bushing engaging features 1202 and 2202 as well as the plate engaging features 1302 and 2302. It also changes the geometry of the threaded insert central hole from its original circular shape to a modified elliptical shape. FIG. 20B shows the assembly with the gap section walls 1702 and 2702 of the first insert section 1002 and second insert section 2002, respectively, set apart from each other. In the preferred embodiment, the maximum gap distance, the term gap distance defined herein as the perpendicular distance between the gap section walls 1702 and 2702, would be equivalent to the amount of material removed from the gap were the insert sections cut from a single piece. For clarification, when the first and second insert sections are placed relative to each other such that the threaded center hole is perfectly circular, i.e., able to accept a circular threaded screw head, the resulting gap distance is at a maximum. This positional configuration increases the linear distance, with respect to the closed distance depicted in FIG. 20A, between the radial extent of the bushing engaging features 1202 and 2202 as well as the plate engaging features 1302 and 2302. It also changes the geometry of the threaded insert central hole from a modified elliptical shape to its original circular shape, thereby readying the threaded hole for acceptance of a threaded screw head.

Figure 21A:
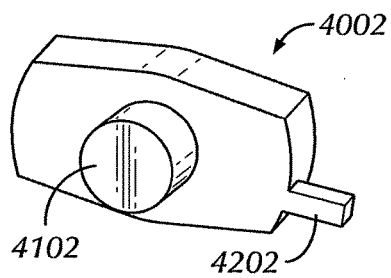
FIG. 21A is an isometric front view of an insert rotation pin.
Figure 21B:
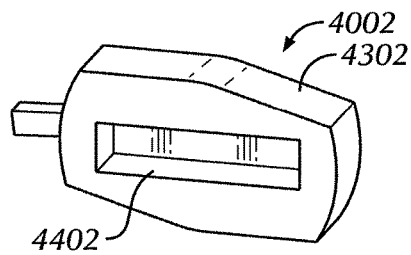
FIG. 21B is an isometric back view of an insert rotation pin.

The tenons 1402 and 2402 are paired on each side of the insert to mate with their mortise counterpart, the insert rotational axel 4002. FIG. 21A shows the front of the insert rotational axel with axel pin 4102 extending from the body. In the preferred embodiment, the body has angled flat surfaces 4302 on the top and bottom as well as a tab 4202 extending to one side. The tab 4202 provides a limit to the amount of rotation allowed when it is assembled with the insert sections and bushing. FIG. 21B shows the back of the rotational axel with the mortise feature 4402 embossed into the body. The mortise feature 4402 is dimensioned to receive both tenons 1402 and 2402, allowing them to translate within the mortise such that the gap distance can be zero, with the insert section walls in contact, or at the defined maximum.

Figure 22:
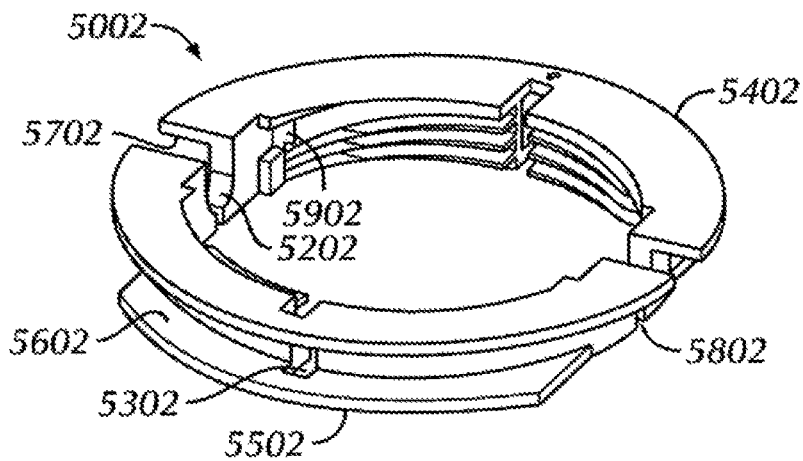
FIG. 22 is an isometric view of a bushing.

The bushing 5002 interfaces with both the insert sections 1002 and 2002 and the surrounding plate. As shown in FIG. 22, the internal surface of the bushing contains insert engaging features 5102 dimensioned to mate with the bushing engaging features 1202 and 2202 of the insert sections. As is described in detail below but not visible in FIG. 22, a flipped mirror image of the visible insert engaging features 5102 are located in the opposite internal wall of the bushing. Two semi-circular cutouts 5202 on opposite sides of the bushing provide a supporting cradle for the insert rotational axel pins 4102. Two insert plate engaging feature cutouts 5302 are located centrally to the insert engaging features 5102. The cutouts are dimensioned to provide a sufficient area for the plate engaging features 1302 and 2302 to rotate about the insert axis, i.e., directed through the rotational axel pin centers, as well as extend radially through the cutouts when the insert sections are separated by the maximum gap distance. The bushing is retained on the plate by the top bushing flange 5402 and the bottom bushing flange 5502. The upper surface 5602 of the bottom bushing flange is in contact with the lower surface of the plate proximate the plate hole thereby preventing the bushing and insert assembly from translating upward through the plate hole. Likewise, the lower surface 5702 of the top bushing flange is in contact with the upper surface of the plate proximate the plate hole thereby preventing the bushing and insert assembly from translating downward through the plate hole. In the preferred embodiment, the bushing is sectioned in two pieces for easier insertion into the plate hole resulting in two small gaps 5802 through the center of the semi-circular cradle 5202. Additionally, a rotation limiting feature 5902 in the inner wall of the bushing 5002 interacts with the insert rotational axel tabs 4202 to prevent rotation of the insert assembly beyond the intended range of rotation.

Figure 23:
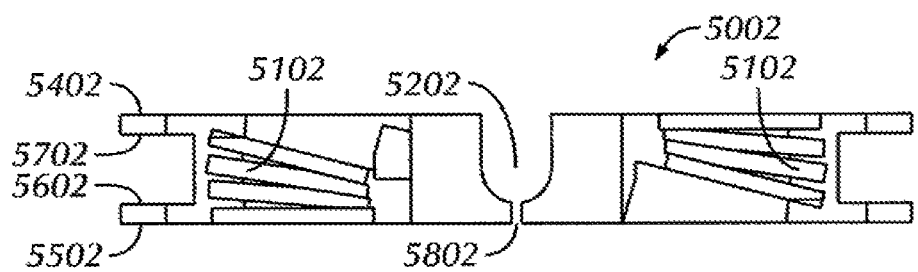
FIG. 23 is a sectioned side view of a bushing, showing engagement features that are complimentary to the engagement features of the first and second insert sections.

The insert engaging features 5102 are more effectively viewed in a side section view as shown in FIG. 23. This view is sectioned through the plate engaging feature cutouts 5302 such that the profiles of the insert engaging features proximate the plate engaging feature cutouts are seen in detail. As can be seen in this view, the insert engaging features 5102 on opposite sides of the bushing sections are inverted mirror images of each other. Likewise, the angles of each slot of the insert engaging feature of the preferred embodiment are dimensioned to allow translation of the bushing engaging features 1202 and 2202 into the slots along a path appropriate to the insert assembly when positioned in the desired rotational angle and translated through the direction of separation of the insert sections as restricted by the insert slide/slot, 1502 and 2502, respectively.

Figure 24:
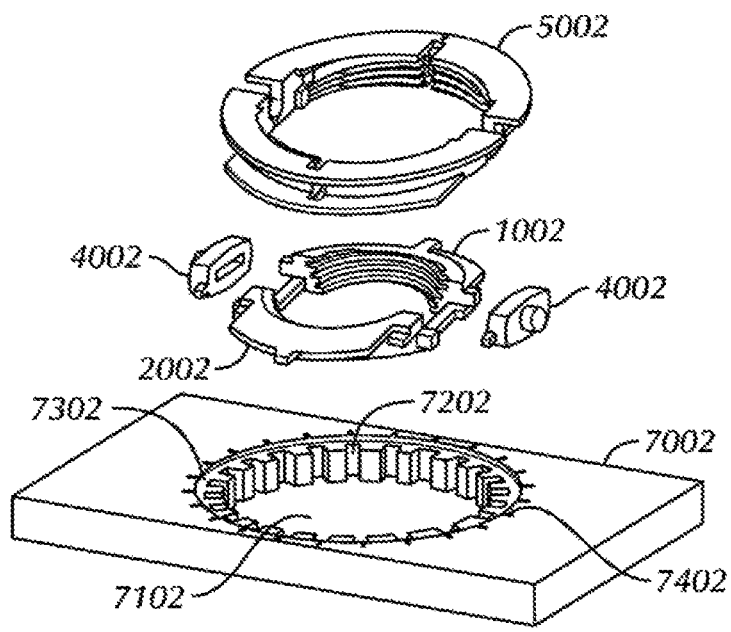
FIG. 24 is an exploded isometric view of the screw locking assembly, including the bushing, first and second insert sections, two rotation pins, and the orthopedic plate.
Figure 27:
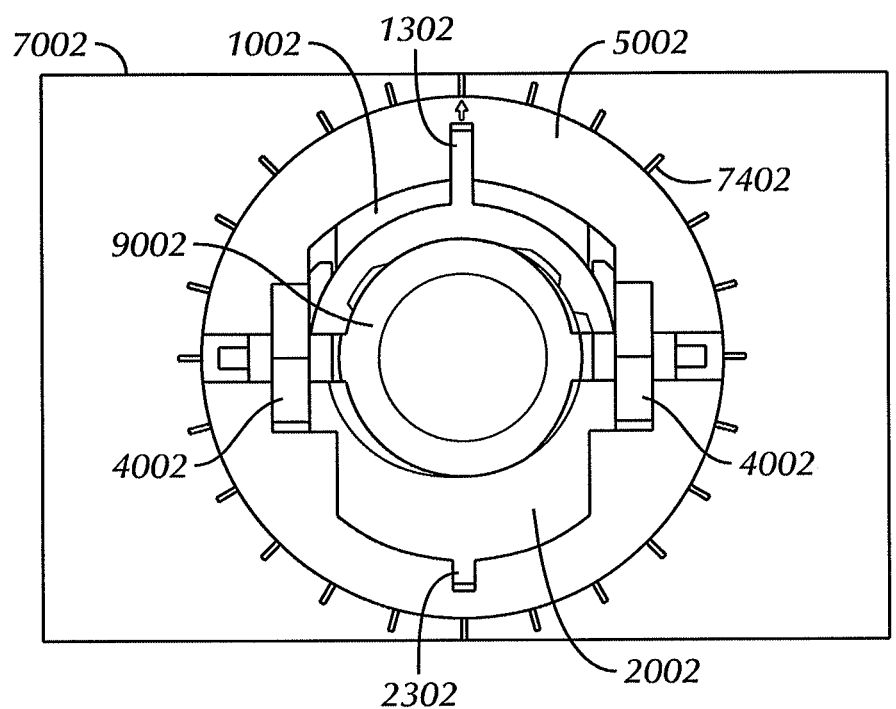
FIG. 27 is a top view of the screw locking assembly with a screw inserted into the threaded insert assembly hole.

A representation of a bone fixation plate 7002 is shown along with an exploded view of the bushing/insert assembly in FIG. 24. The plate hole 7102 into which the bushing 5002 is placed includes insert tab engaging features 7202 distributed around the circumference of the hole. Upon expanding the insert sections to the maximum gap distance, the plate engaging features 1302 and 2302 of the first and second insert sections each extend into one of two insert tab engaging features located 180 degrees apart along the circumference of the plate hole 7102. In the preferred embodiment shown, there are twenty-four tab engaging features providing for radial directional orientations of the screw around the hole circumference in fifteen degree increments. As previously indicated, it is contemplated that other means for engaging and restricting motion between the insert sections and the plate would provide the same intended function as the flange and flange receiving features of the preferred embodiment. The preferred embodiment of the plate includes a recessed shelf 7302 circumscribing the perimeter of the plate hole 7102. Not shown in FIG. 24 is the bottom surface of the plate which also includes an equivalent bottom recessed shelf. The recessed shelf is dimensioned to receive the top and bottom bushing flanges, 5402 and 5502, respectively. Thereby, the bushing is held within the plate hole 7102 but maintain rotational freedom about the common center axis of the bushing and plate hole. It is contemplated that the single degree of rotational freedom of the bushing relative to the plate would also be accomplished without the top and bottom recessed shelves 7302 The recessed shelves provide a means for the top and bottom bushing flanges 5402 and 5502 to be positioned below the plate surface thereby placing the upper surface 7502 of the bushing top flange and the lower surface 7602 of the bushing bottom flange level with the top and bottom plate surfaces, respectively. Also distributed about the perimeter of the plate hole are indicators 7402 aligned with the insert tab engaging features 7202 for assisting in directional orientation of the bushing, thereby providing guidance to determine the resulting direction of a screw placed at an angle within the hole.

The interaction between engaging features of the insert sections and the bushing enable the insert sections to be rigidly locked at a fixed angle about the insert axis, i.e., directed through the rotational axel pin 4102 centers, relative to the bushing. As is shown in FIGS. 25A-25C, the distance between the gap section walls 1702 and 2702, and the rotational angle of the insert sections relative to the bushing combine to provide a locked state and an unlocked state between the insert sections and the bushing, as well as a locked state and an unlocked state between the insert sections and the plate. FIG. 25A shows the insert sections 1002 and 2002 positioned with the gap section walls 1702 and 2702 in contact, thereby creating separation between the bushing engaging features of the insert sections 1202 and 2202, and the insert engaging features of the bushing 5102. In this state, the insert assembly is unlocked and free to rotate about the insert axis relative to the bushing. Additionally, the plate engaging features of the insert sections 1302 and 2302 are positionally separated from the insert tab engaging features of the plate 7202. In this state, the insert/bushing assembly is unlocked and free to rotate about the central hole axis of the plate.

FIG. 25B shows the insert sections 1002 and 2002 positioned, relative to each other, with the gap section walls 1702 and 2702 at the maximum gap distance, thereby engaging the bushing engaging features of the insert sections 1202 and 2202, and the insert engaging features of the bushing 5102. In this state, the insert assembly is locked and restricted from rotation about the insert axis relative to the bushing. Additionally, the plate engaging features of the insert sections 1302 and 2302 are engaged with the insert tab engaging features of the plate 7202. In this state, the insert/bushing assembly is also locked and restricted from rotation about the central hole axis of the plate.

Functional use of the variable angle screw locking mechanism described herein follows the process described below for an orthopedic application where by the steps include setting the desired direction of the screw, locking the direction relative to the plate, and inserting the screw for fixation of the bone to the plate. A bone fixation plate containing the invention described herein is placed on a bone to be secured to the plate with screws. With the gap section walls of the insert 1702 and 2702 in contact and central to the bushing circumference, thereby placing the insert/bushing/plate assembly in an unlocked state, the insert/bushing assembly is rotated about the plate hole central axis to the desired radial direction about the plate hole circumference. The insert assembly is then rotated about the insert axis until the desired angle of the insert threaded hole, relative to the plate top surface, is reached. In the preferred embodiment, the insert/bushing engaging features allow for such angles of zero, five, ten, and fifteen degrees. The insert sections 1002 and 2002 are then separated such that the gap section walls 1702 and 2702 are at the maximum gap distance, thereby engaging the plate and bushing engaging features 1202, 2202, and 5102, respectively. A drill guide, not described herein but common to orthopedic plate instrumentation and known to those skilled in the art, is then placed in the threaded hole in alignment with the central axis of the threaded hole. The bone is appropriately drilled for the screw to be placed therein. The drill guide is then removed and the screw is screwed into the bone until the screw head initiates contact with the insert assembly. The screw head is then threaded into the insert threaded hole thereby fixing the gap section walls 1702 and 2702 at the maximum gap distance. The insert/bushing assembly and the bone screw are thusly locked at the angle and radial direction that was set. As an example, if the desired angle of the screw relative to the plate surface was ten degrees, the insert assembly would be locked in the preferred embodiment as shown in FIG. 25C.

Another feature that is incorporated into the design of the insert sections prevents any portion of the insert section geometry from extending above or below the plate surface. In many orthopedic clinical situations where tissue coverage of the fixation site is minimal or there is a possibility of heightened sensitivity, extraneous projections above the bone are not well tolerated and usually efforts are made to avoid such projections. Referring to FIG. 26A, the insert/bushing/plate assembly is shown with a screw 9002 locked in place at a zero degree angle with respect to the plate upper surface 9302. In this state, it can be seen that the second insert section upper surface 9102 is level with both the bushing upper surface 9202 and the plate upper surface 9302. Also shown is the upper surface of the first insert section 9402, which is angled from the first insert section upper surface by an amount equivalent to the maximum rotational angle by which the insert/bushing engaging features allow for locking. In the preferred embodiment, this angle is fifteen degrees.

Now referring to FIG. 26B, the insert/bushing/plate assembly is shown with a screw 9002 locked in place at a fifteen degree angle with respect to the plate upper surface 9302. In this state, it can be seen that the first insert section upper surface 9402 is level with both the bushing upper surface 9202 and the plate upper surface 9302. Because the first insert section upper surface 940 and the second insert section upper surface 9102 are at a fifteen degree angle relative to each other, the upper surface 9102 of the second insert section is seen angled below the upper plate surface 9302 by fifteen degrees. Likewise, but not shown in FIG. 26A or 26B, the lower surfaces of the first and second insert sections 1002 and 2002 are flipped mirror images of the corresponding upper surfaces. Therefore, within the range of the minimum, i.e., zero, and maximum, i.e., fifteen, degree rotational angles of the insert assembly relative to the bushing, both the upper surfaces and lower surfaces of the insert assembly remain level with or below the upper and lower plate surfaces.

A similar aspect of the invention includes features that position the screw head 9502 within the insert such that no portion of the head extends above the upper surface of the plate 9302. In the preferred embodiment, the screw head shape is complimentary to the threaded hole shape such that upon threading the screw head into the threaded hole, the geometry limits the insertion of the screw head at a depth that positions the top of the screw head 9502 at the level of the upper surface 9402 of the first insert section. Thus when the insert assembly and screw are positioned at the maximum rotation angle, as shown in FIG. 26B, the all portions of the screw head are at or below the upper surface 9302 of the plate. In the preferred embodiment, the profile of the threaded hole of the insert assembly follows a beveled curve, narrowing in diameter closer to the lower surface of the insert assembly. The sectioned profile views of the insert threaded hole in FIG. 25A-25C show such a beveled profile. Consequently, the screw head profile may be similarly beveled or tapered in a manner sufficient to allow full insertion of the screw head into the threaded hole but prevent further insertion at the point where the screw head 9502 is at or below the level of the first insert section upper surface. It is contemplated that other shape profiles may be equally sufficient for this purpose, for example a straight tapered or conical hole shape with an equally tapered or conical screw head profile.

Additionally, such a beveled or tapered threaded hole profile would be sufficient to accept a non-threaded screw which would not lock to the plate. Such constructs are utilized in clinical orthopedic situations where it is desirable to draw, or lag the underlying bone up to the plate and/or fix the bone to the plate without the rigidity of a locked screw. In such circumstances, the insert/bushing/plate assembly would be locked from rotation, however the non-threaded screw could be placed into the bone at any angle and radial direction relative to the plate, given sufficient clearance of the screw shaft within the insert bottom opening.

In the preferred embodiment, the orthopedic plate is provided in such a manner that the insert sections, rotational axels, and bushing are pre-assembled in the plate hole(s) and ready for immediate use. It is contemplated that the insert sections, rotational axels, and bushing may be assembled as a sub-assembly that is provided as a kit, packaged with bone plates or separately as an accessory to the plates, such that one or more sub-assemblies can be inserted into the plate only in the holes intended to be used for variable angle locking of screws. It is also contemplated that the plate holes may be fashioned such that they are usable for fixed angle locking, e.g., with the interior hole wall threaded, or non-locking constructs without the insertion of the sub-assembly. Therefore, a plate with features adequate to support the sub-assembly as well as fixed angle or non-locking constructs could be fashioned at will and at or just before the time of surgery in an arrangement that is customized for the specific application.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

I claim:

1. An orthopedic bone fixation assembly for connecting to a bone or bone fragments of a patient, the orthopedic bone fixation assembly comprising:

a fixation plate having a hole therein, the fixation plate including an upper surface and an opposing lower surface for positioning proximate at least one of the bone and bone fragments, a shoulder recessed from the upper surface and a cylindrical-shaped aperture extending therethrough in a direction from the upper surface to the lower surface;

an insert removably securable to the hole, the insert including a base portion, an insert hole and a flange extending laterally outwardly from an upper end of the base portion, the insert defining an insert central axis extending in a direction generally perpendicular to the flange; and a screw removably securable to the insert, the screw having a screw head, the insert hole having internal threads for threadingly engaging the screw, the insert hole defining an insert thread axis extending in a direction offset by an offset angle relative to the insert central axis such that threaded engagement between the screw and the insert hole offsets a longitudinal axis of the screw from the insert central axis by the offset angle, the flange of the insert including a marking to indicate an orientation of the insert thread axis, the aperture of the fixation plate being dimensioned to complementarily, removably receive the base portion of the insert and the recessed shoulder being dimensioned to complementarily, removably receive the flange of the insert, the insert being configured for engagement with the fixation plate in a plurality of rotational orientations about the insert central axis to selectively orient the direction of the insert thread axis, and subsequent threading of the screw with the insert, through the fixation plate and into at least one of the bone and bone fragments secures the assembly to the at least one of the bone and bone fragments and orients the longitudinal axis of the screw into the underlying at least one of the bone and bone fragments along the insert thread axis.

2. The orthopedic bone fixation assembly of claim 1, wherein the base portion of the insert further includes a plurality of tabs extending laterally outwardly from an exterior surface thereof, and an inner surface of the fixation plate, defining the aperture, includes a plurality of generally L-shaped insertion grooves each having a substantially vertical insertion groove component and an intersecting substantially horizontal locking groove component, the tabs of the base portion of the insert being configured for downward translation through the substantially vertical insertion groove components, respectively, for mating of the insert with the fixation plate, and the insert being subsequently rotatable relative to the fixation plate about the insert central axis to slide the tabs through the substantially horizontal locking groove components, respectively, and lock the insert with the fixation plate.

3. The orthopedic bone fixation assembly of claim 2, wherein the insert is rotatable relative to the fixation plate about the insert central axis in a clockwise direction to slide the tabs through the substantially horizontal locking groove components, respectively, and lock the insert with the fixation plate.

4. The orthopedic bone fixation assembly of claim 3, wherein the insert is rotatable relative to the fixation plate about the insert central axis in a counter-clockwise direction to slide the tabs through the substantially horizontal locking groove components, respectively, toward the respective substantially vertical insertion groove components, respectively, and re-align the tabs with the substantially vertical insertion groove components, respectively, and the tabs are withdrawn through the substantially vertical insertion groove components, respectively, for removal of the insert from the fixation plate.

5. The orthopedic bone fixation assembly of claim 2, wherein the fixation plate includes an equal number of generally L-shaped insertion grooves as tabs of the insert.

6. The orthopedic bone fixation assembly of claim 2, wherein the upper surface of the fixation plate includes markings corresponding to the L-shaped insertion grooves to generally indicate selectable directions for orienting the direction of the insert thread axis according to a rotational orientation of the insert relative to the fixation plate.

7. The orthopedic bone fixation assembly of claim 1, wherein the flange of the insert is substantially flush with the upper surface of the fixation plate upon full mating of the insert with the fixation plate.

8. The orthopedic bone fixation assembly of claim 1, wherein the offset angle is between about 0 and about 25 degrees.

9. The orthopedic bone fixation assembly of claim 1, wherein the insert hole defines an inward taper such that a diameter of the insert hole adjacent the flange is larger than a diameter of the insert hole at an opposing end of the insert hole, thereby creating an interference fit between the head of the screw and the insert when head is fully threaded into the insert hole.

10. The orthopedic bone fixation assembly of claim 9, wherein the base portion of the insert includes a plurality of relief grooves, recessed from a bottom end of the base portion and angularly spaced about the insert hole, dividing the base portion into a plurality of angularly spaced base portion segments, the plurality of base portion segments being radially outwardly expandable into increased frictional surface contact with the fixation plate by fully threading the screw head into the insert hole.

11. The orthopedic bone fixation assembly of claim 1, further comprising a drill guide removably engageable with the insert for engaging the insert with the fixation plate.

12. The orthopedic bone fixation assembly of claim 11, wherein the insert flange includes a plurality of recesses in an upper surface thereof and the drill guide includes a plurality of legs substantially fittingly engageable with the recesses of the flange.

13. The orthopedic bone fixation assembly of claim 12, wherein the drill guide includes a central cannula, and the legs of the drill guide define unequal lengths, the respective lengths being configured to align the central cannula of the drill guide with the insert thread axis upon engagement with the recesses of the flange.

* * * * *